(12) United States Patent
Dacosta et al.

(10) Patent No.: US 12,171,442 B2
(45) Date of Patent: Dec. 24, 2024

(54) FUSION SYSTEMS, INSTRUMENTS, BONE PLATES AND METHODS OF USE

(71) Applicant: Paragon 28, Inc., Englewood, CO (US)

(72) Inventors: Albert Dacosta, Lone Tree, CO (US); Laura Zagrocki Brinker, Lone Tree, CO (US); Richard David Hunt, Arvada, CO (US); Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 461 days.

(21) Appl. No.: 17/446,358

(22) Filed: Aug. 30, 2021

(65) Prior Publication Data

US 2021/0386437 A1 Dec. 16, 2021

Related U.S. Application Data

(63) Continuation of application No. PCT/US2020/020501, filed on Feb. 28, 2020.
(Continued)

(51) Int. Cl.
 *A61B 17/17* (2006.01)
 *A61B 17/66* (2006.01)
(Continued)

(52) U.S. Cl.
 CPC .......... *A61B 17/1775* (2016.11); *A61B 17/66* (2013.01); *A61B 17/8019* (2013.01);
(Continued)

(58) Field of Classification Search
 CPC . A61B 17/1775; A61B 17/6425; A61B 17/66; A61B 2017/681; A61B 17/8019;
(Continued)

(56) References Cited

U.S. PATENT DOCUMENTS 2,434,431 A * 1/1948 Pincock ................. A61B 17/17
 606/104
2,526,959 A 10/1950 Lorenzo
(Continued)

FOREIGN PATENT DOCUMENTS

| EP | 0617927 | 10/1994 |
|----|---------|---------|
| EP | 1273271 | 8/2007 |

(Continued)

OTHER PUBLICATIONS

International Search Report and Written Opinion of the International Searching Authority for PCT/US2020/020501, May 6, 2020, 11 pages.
(Continued)

*Primary Examiner* — Larry E Waggle, Jr.
(74) *Attorney, Agent, or Firm* — Heslin Rothenberg Farley & Mesiti P.C.; Jacquelyn A. Graff, Esq.

(57) ABSTRACT

Instruments, implants, bone plates, systems and methods for correcting bone deformities and fractures in the lower extremity and applying compression across joints to be fused are disclosed. Specifically, targeting instruments, implants, bone plates, systems and methods used for correcting bone deformities and/or fractures in the foot and applying compression across joints to be fused are disclosed.

20 Claims, 39 Drawing Sheets

Related U.S. Application Data

(60) Provisional application No. 62/812,132, filed on Feb. 28, 2019.

(51) Int. Cl.
*A61B 17/68* (2006.01)
*A61B 17/80* (2006.01)

(52) U.S. Cl.
CPC ........ *A61B 17/8061* (2013.01); *A61B 17/808* (2013.01); *A61B 2017/681* (2013.01)

(58) Field of Classification Search
CPC .............. A61B 17/8061; A61B 17/808; A61B 17/8866; A61B 17/8872
See application file for complete search history.

(56) References Cited

U.S. PATENT DOCUMENTS

| | | | |
|---|---|---|---|
| 3,709,219 | A | 1/1973 | Halloran |
| 4,483,334 | A | 11/1984 | Murray |
| 4,624,249 | A * | 11/1986 | Alvarez Cambras ........................ A61B 17/6441 606/57 |
| 4,790,302 | A | 12/1988 | Colwill |
| 5,098,435 | A | 3/1992 | Stednitz |
| 5,350,380 | A | 9/1994 | Goble |
| 5,352,228 | A | 10/1994 | Kummer |
| 5,429,641 | A | 7/1995 | Gotfried |
| 5,458,602 | A | 10/1995 | Goble |
| 5,688,284 | A | 11/1997 | Chervitz |
| 6,342,057 | B1 | 1/2002 | Brace |
| 6,692,496 | B1 | 2/2004 | Wardlaw |
| 7,011,665 | B2 | 3/2006 | Null |
| 7,311,711 | B2 * | 12/2007 | Cole ...................... A61B 17/66 606/57 |
| 7,316,687 | B2 | 1/2008 | Aikins |
| 7,785,326 | B2 | 8/2010 | Green |
| 7,819,877 | B2 | 10/2010 | Guzman |
| 8,206,389 | B2 | 6/2012 | Huebner |
| 8,231,627 | B2 | 7/2012 | Huebner |
| 8,337,503 | B2 | 12/2012 | Lian |
| 8,535,355 | B2 | 9/2013 | Prasad |
| 8,821,508 | B2 | 9/2014 | Medoff |
| 9,044,250 | B2 | 6/2015 | Olsen |
| 9,119,721 | B2 | 9/2015 | Sharkey |
| 9,161,796 | B2 | 10/2015 | Chiodo |
| 9,241,744 | B2 | 1/2016 | Blake |
| 9,421,103 | B2 | 8/2016 | Jeng |
| 10,327,829 | B2 | 6/2019 | DaCosta |
| 10,441,317 | B2 * | 10/2019 | DeVasConCellos ........................ A61B 17/1615 |
| 2002/0161443 | A1 | 10/2002 | Michelson |
| 2003/0009217 | A1 | 1/2003 | McKernan |
| 2004/0102776 | A1 | 5/2004 | Huebner |
| 2004/0102777 | A1 | 5/2004 | Huebner |
| 2004/0181221 | A1 | 9/2004 | Huebner |
| 2004/0193165 | A1 | 9/2004 | Orbay |
| 2005/0033301 | A1 | 2/2005 | Lombardo |
| 2005/0059968 | A1 | 3/2005 | Grant |
| 2005/0234472 | A1 | 10/2005 | Huebner |
| 2006/0069394 | A1 | 3/2006 | Weiler |
| 2006/0189996 | A1 | 8/2006 | Orbay |
| 2006/0264944 | A1 | 11/2006 | Cole |
| 2007/0173843 | A1 | 7/2007 | Matityahu |
| 2007/0225714 | A1 | 9/2007 | Gradl |
| 2007/0239168 | A1 | 10/2007 | Kuenzi |
| 2007/0265634 | A1 | 11/2007 | Weinstein |
| 2007/0270850 | A1 | 11/2007 | Geissler |
| 2008/0015590 | A1 | 1/2008 | Sanders |
| 2008/0091197 | A1 | 4/2008 | Coughlin |
| 2008/0188852 | A1 | 8/2008 | Matityahu |
| 2009/0036931 | A1 | 2/2009 | Pech |
| 2009/0062797 | A1 | 3/2009 | Huebner |
| 2009/0088767 | A1 | 4/2009 | Leyden |
| 2009/0093849 | A1 | 4/2009 | Grabowski |
| 2009/0157086 | A1 | 6/2009 | Digeser |
| 2010/0087824 | A1 | 4/2010 | Collazo |
| 2010/0121324 | A1 | 5/2010 | Tyber |
| 2010/0179597 | A1 | 7/2010 | Henderson |
| 2011/0046681 | A1 | 2/2011 | Prandi |
| 2011/0093018 | A1 | 4/2011 | Prasad |
| 2011/0125200 | A1 | 5/2011 | Hanson |
| 2011/0144647 | A1 | 6/2011 | Appenzeller |
| 2011/0144700 | A1 | 6/2011 | Konieczynski |
| 2011/0152955 | A1 | 6/2011 | Keller |
| 2011/0218576 | A1 | 9/2011 | Galm |
| 2011/0224734 | A1 | 9/2011 | Schelling |
| 2011/0264149 | A1 | 10/2011 | Pappalardo |
| 2011/0270319 | A1 | 11/2011 | Sheffer |
| 2011/0282397 | A1 | 11/2011 | Richter |
| 2012/0078252 | A1 | 3/2012 | Huebner |
| 2012/0209268 | A1 | 8/2012 | Overes |
| 2012/0253347 | A1 | 10/2012 | Murashko, Jr. |
| 2012/0271314 | A1 | 10/2012 | Stemniski |
| 2012/0303038 | A1 | 11/2012 | Durante |
| 2012/0316562 | A1 | 12/2012 | Costa |
| 2013/0046311 | A1 | 2/2013 | Blake |
| 2013/0150903 | A1 | 6/2013 | Vincent |
| 2013/0172942 | A1 | 7/2013 | Lewis et al. |
| 2013/0231668 | A1 | 9/2013 | Olsen |
| 2013/0325076 | A1 | 12/2013 | Palmer |
| 2014/0066996 | A1 | 3/2014 | Price et al. |
| 2014/0107798 | A1 | 4/2014 | Jeng et al. |
| 2014/0114322 | A1 | 4/2014 | Perez, III |
| 2014/0180348 | A1 | 6/2014 | Thoren et al. |
| 2014/0257312 | A1 | 9/2014 | Solitario, Jr. |
| 2015/0032168 | A1 | 1/2015 | Orsak |
| 2015/0150683 | A1 | 6/2015 | Donner et al. |
| 2015/0182267 | A1 | 7/2015 | Wolf et al. |
| 2015/0238227 | A1 | 8/2015 | Singh et al. |
| 2015/0245923 | A1 | 9/2015 | Abdou |
| 2015/0289904 | A1 | 10/2015 | Thoren et al. |
| 2015/0359580 | A1 | 12/2015 | Dacosta et al. |
| 2016/0030064 | A1 | 2/2016 | Dacosta et al. |
| 2016/0135858 | A1 | 5/2016 | Dacosta et al. |
| 2016/0235414 | A1 | 8/2016 | Hatch et al. |
| 2016/0242791 | A1 | 8/2016 | Fallin et al. |
| 2016/0310191 | A1 | 10/2016 | Seykora |
| 2016/0324552 | A1 | 11/2016 | Baker et al. |
| 2016/0354128 | A1 | 12/2016 | Jeng |
| 2017/0000534 | A1 | 1/2017 | Medoff |
| 2017/0056031 | A1 | 3/2017 | Awtrey et al. |
| 2017/0100175 | A1 | 4/2017 | Dacosta |
| 2017/0216043 | A1 | 8/2017 | Surma et al. |
| 2018/0110530 | A1 | 4/2018 | Wagner et al. |
| 2018/0242987 | A1 | 8/2018 | Lintula et al. |
| 2018/0242988 | A1 | 8/2018 | Dacosta et al. |
| 2018/0271507 | A1 | 9/2018 | Gasser |
| 2018/0280069 | A1 | 10/2018 | Barmes et al. |
| 2019/0015140 | A1 | 1/2019 | Dacosta et al. |
| 2019/0038326 | A1 | 2/2019 | Hedgeland et al. |
| 2021/0128177 | A1 | 5/2021 | Lintula et al. |

FOREIGN PATENT DOCUMENTS

| | | |
|---|---|---|
| EP | 2745786 | 6/2014 |
| EP | 3023068 | 5/2016 |
| FR | 3030221 | 6/2016 |
| JP | 04250156 | 9/1992 |
| JP | 2002534150 | 10/2002 |
| JP | 2009112594 | 5/2009 |
| JP | 2014511200 | 5/2014 |
| JP | 2015515346 | 5/2015 |
| JP | 2016528993 | 9/2016 |
| JP | 2019509132 | 4/2019 |
| WO | 1994015556 | 7/1994 |
| WO | 2005089660 | 9/2005 |
| WO | 2009052294 | 4/2009 |
| WO | 2012103335 | 8/2012 |
| WO | 2012106477 | 8/2012 |
| WO | 2013009574 | 1/2013 |
| WO | 2015094409 | 6/2015 |

(56) References Cited

FOREIGN PATENT DOCUMENTS

| WO | 2015138542 | 9/2015 |
|---|---|---|
| WO | 2017004221 | 1/2017 |
| WO | 2017011656 | 1/2017 |

OTHER PUBLICATIONS

Budny et al. "Naviculocuneiform Arthrodesis," Clinics in Podiatric Medicine and Surgery, vol. 24, pp. 753-763, Oct. 2007.

Kamat et al. "Laparoscopic extraction of fractured Kirschner wire from the pelvis," Journal of Minimal Access Surgery, vol. 10, No. 2, pp. 97-98, Jun. 2014.

\* cited by examiner

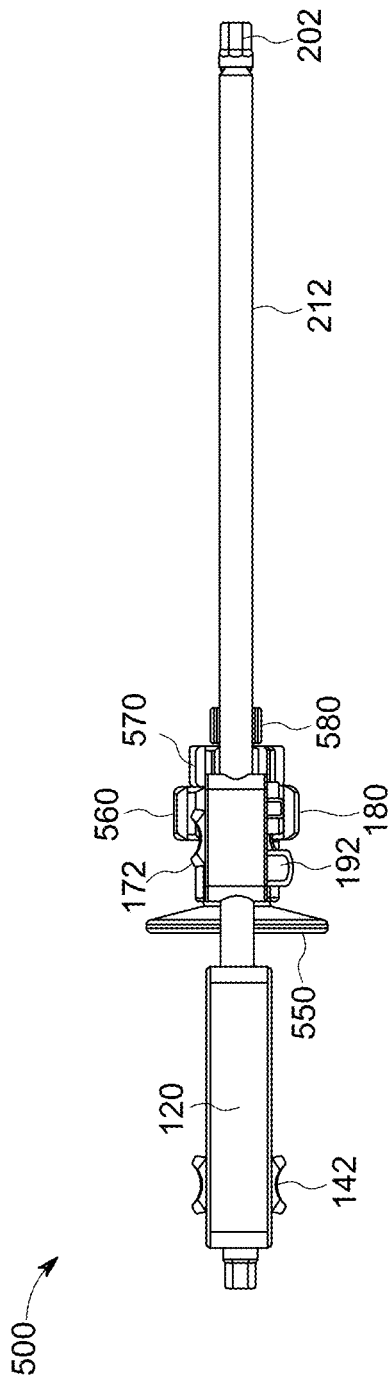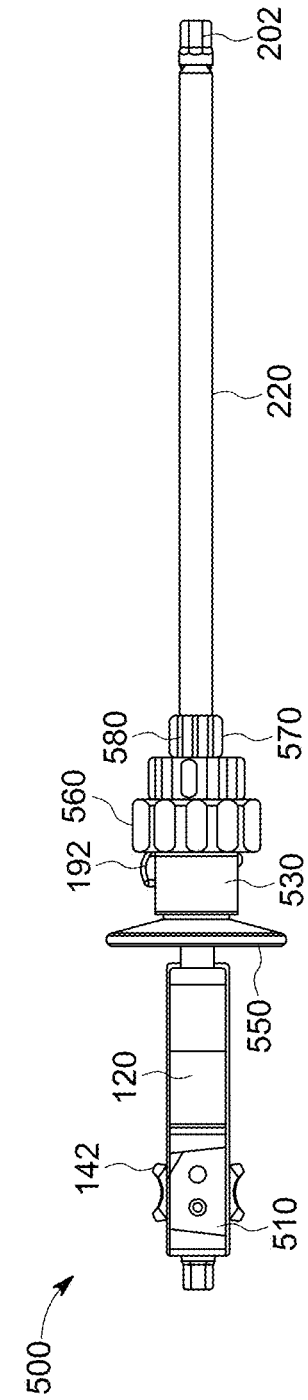
FIG. 32
FIG. 33

FUSION SYSTEMS, INSTRUMENTS, BONE PLATES AND METHODS OF USE

CROSS REFERENCE TO RELATED APPLICATION

This application is a continuation of PCT/US2020/020501 filed Feb. 28, 2020 and entitled Fusion Systems, Instruments, Bone Plates and Methods of Use, which claims priority benefit under 35 U.S.C. § 119(e) of U.S. provisional application No. 62/812,132 filed Feb. 28, 2019, entitled Fusion Systems, Instruments, Bone Plates and Methods of Use, which is incorporated herein by reference in its entirety.

FIELD OF THE INVENTION

The present invention relates generally to general surgery, podiatric, and orthopaedic instruments used for correcting bone deformities. More specifically, but not exclusively, the present invention relates to instruments, implants, plates, systems and methods for correcting bone deformities and applying compression across joints to be fused.

BACKGROUND OF THE INVENTION

Many currently available instruments used in conjunction with implants for correcting bone deformities and fractures use various mechanisms. The currently available instruments may experience problems with inaccurate targeting and instability. Thus, new instruments and methods of use are needed to ensure proper and reproducible orientation of corrective or stabilization devices to be implanted into the foot and ankle.

SUMMARY OF THE INVENTION

Aspects of the present invention provide instruments, implants, plates, systems and methods for correcting bone deformities in the foot.

In one aspect, provided herein is a joint compression device. The joint compression device includes a base system and at least one arm coupled to the base system.

In another aspect, provided herein is are methods of using the joint compression devices.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 32 is a first side view of the joint compression device of FIG. 28, in accordance with an aspect of the present disclosure;

FIG. 33 is a second side view of the joint compression device of FIG. 28, in accordance with an aspect of the present disclosure;

DETAILED DESCRIPTION FOR CARRYING OUT THE INVENTION

Figure 1:
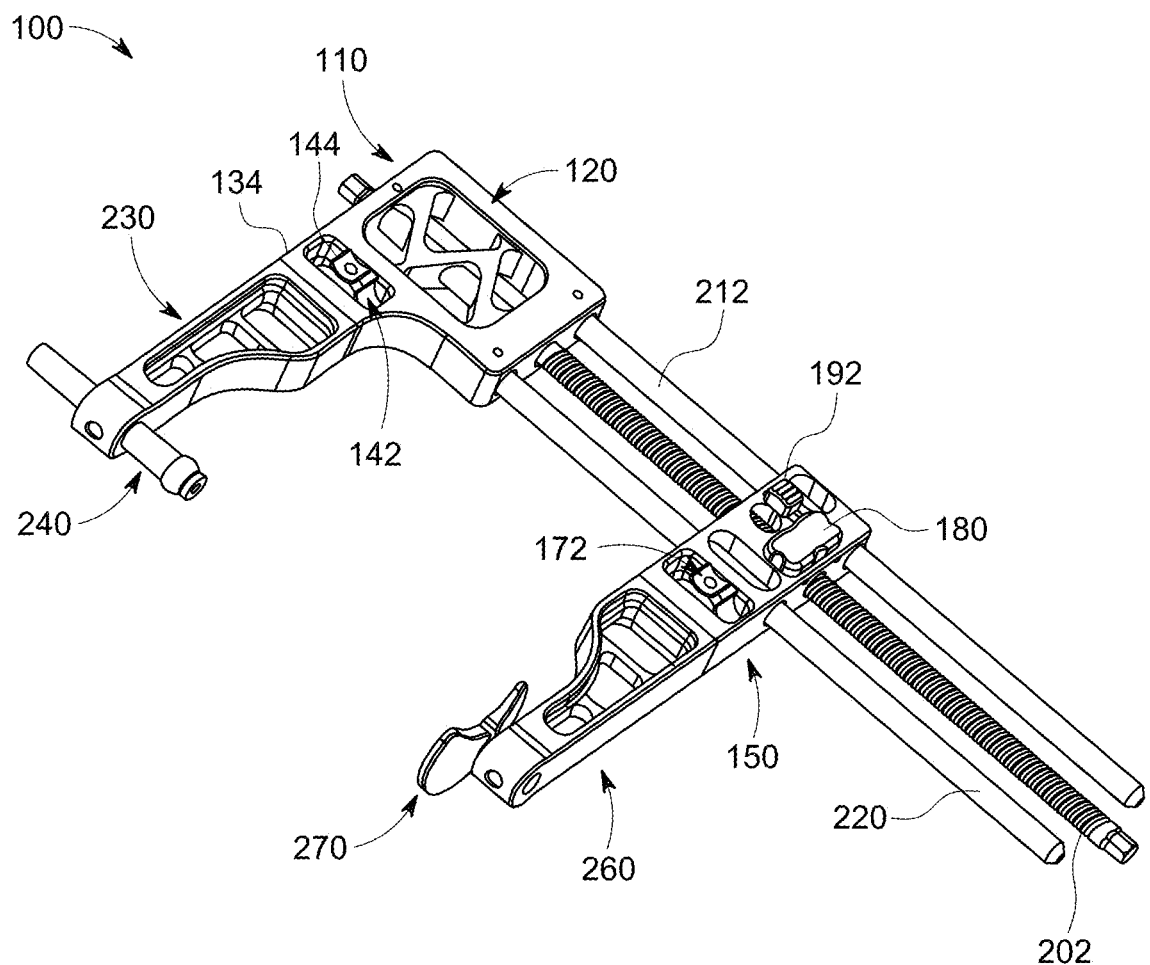
FIG. 1 is a first perspective view of one embodiment of a joint compression device, in accordance with an aspect of the present disclosure.
Figure 2:
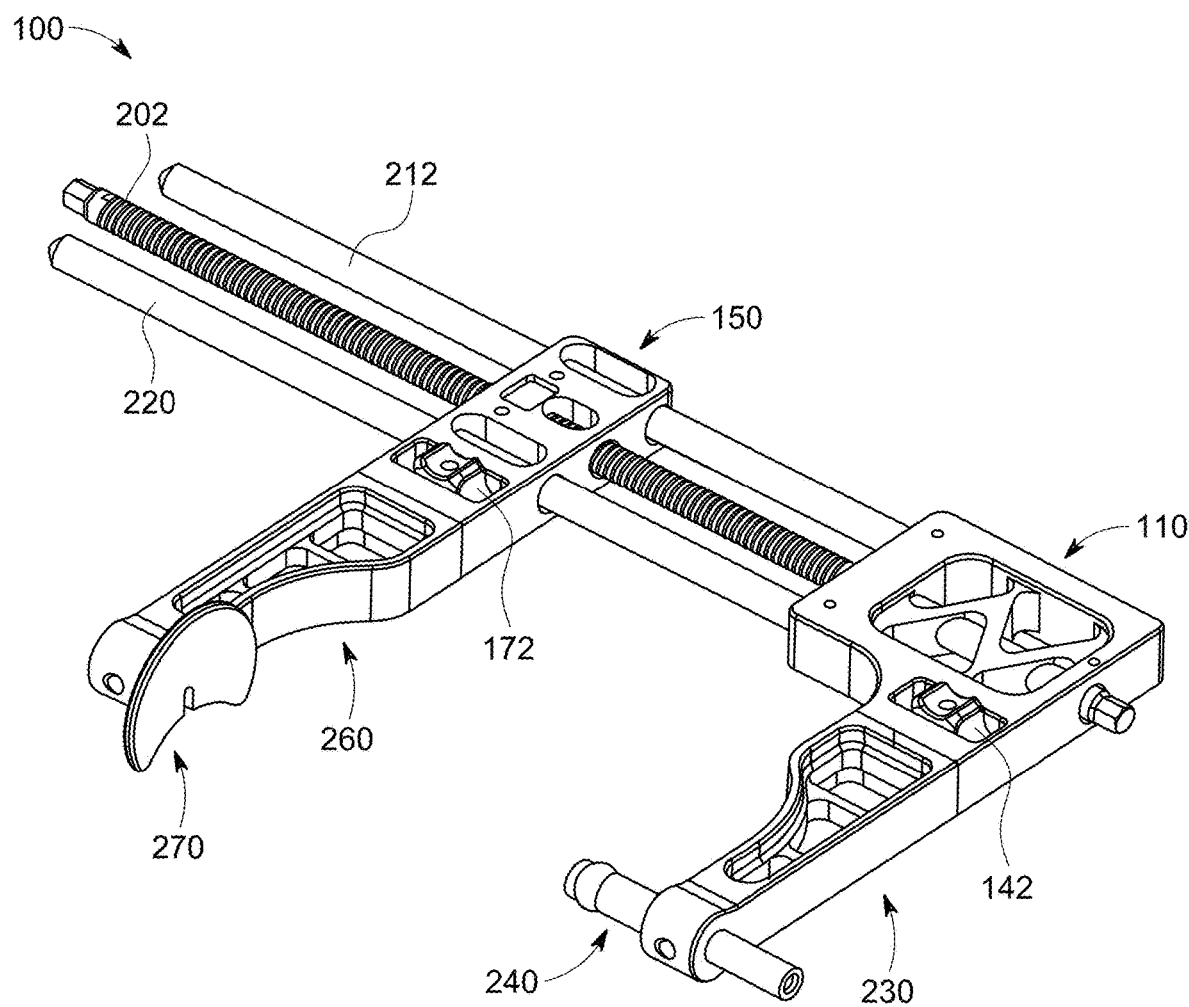
FIG. 2 is a second perspective view of the joint compression device of FIG. 1, in accordance with an aspect of the present disclosure.

Generally stated, disclosed herein are instruments, implants, plates, and systems for correcting bone deformities and applying compression across one or more joints to be fused. Further, methods for correcting bone deformities using instruments, implants, plates, and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Referring now to FIGS. 1-47, plate fusion systems or joint compression devices 100, 400, 500, 700, 800 are shown. The joint compression devices 100, 400, 500, 700, 800 may each be used to apply compression across joints to be fused. Each joint compression device 100, 400, 500, 700, 800 includes a base system or parallel bar compression system 110, 710. The joint compression devices 100, 400, 500 include the base system 110 and the joint compression devices 700, 800 include the base system 710. The base system 110 includes a first member or parallel bar rack 120, a second member or threaded engagement block 150, a translating member or lead screw 202, a first bar 212, and a second bar 220, as shown in at least FIGS. 1, 15 and 28. The first member 120 is coupled to the second member 150 by the translating member 202, the first bar 212 and the second bar 220. The translating member 202, first bar 212 and second bar 220 extend between the first member 120 and the second member 150 positioned parallel to each other.

Figure 3:
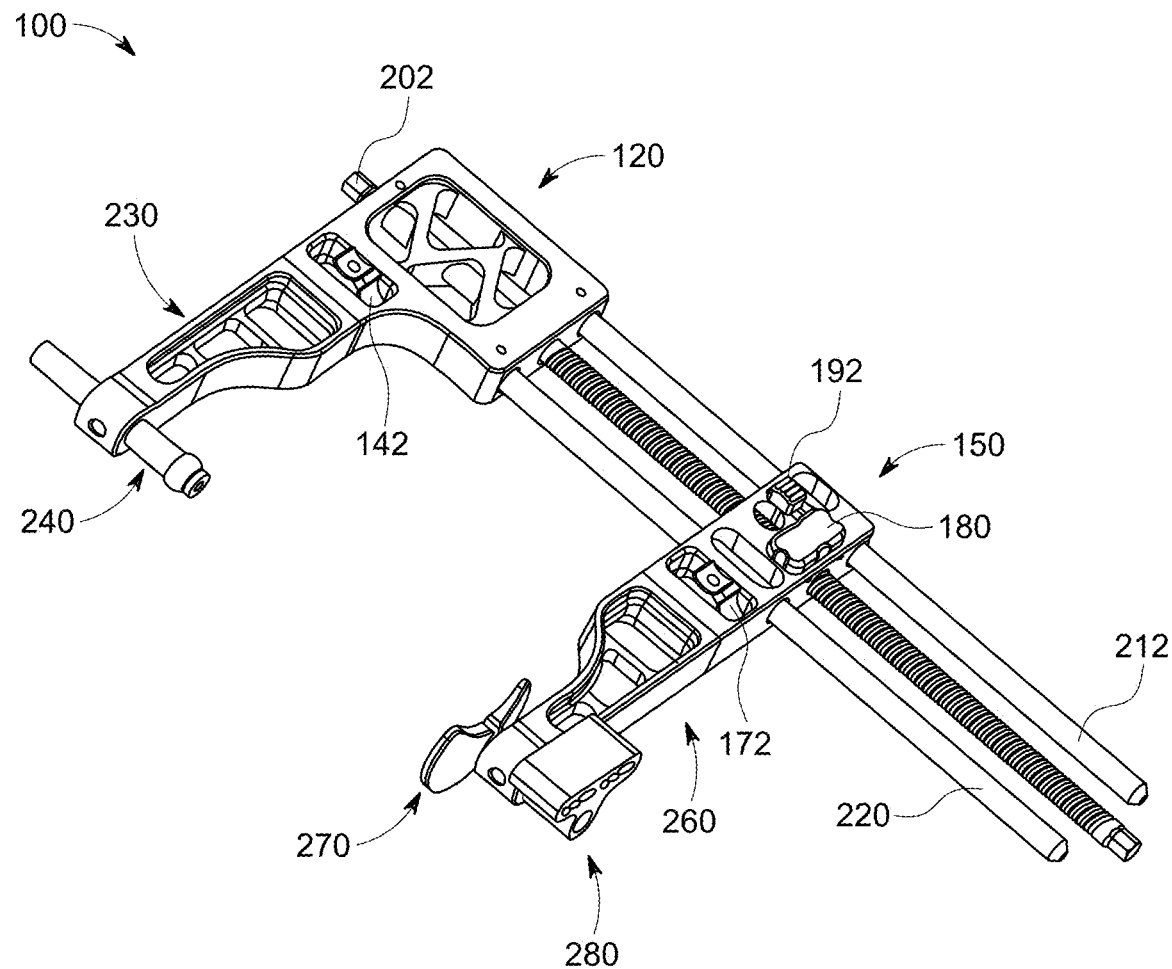
FIG. 3 is a first perspective view of the joint compression device of FIG. 1 with a k-wire guide attached, in accordance with an aspect of the present disclosure.
Figure 4:
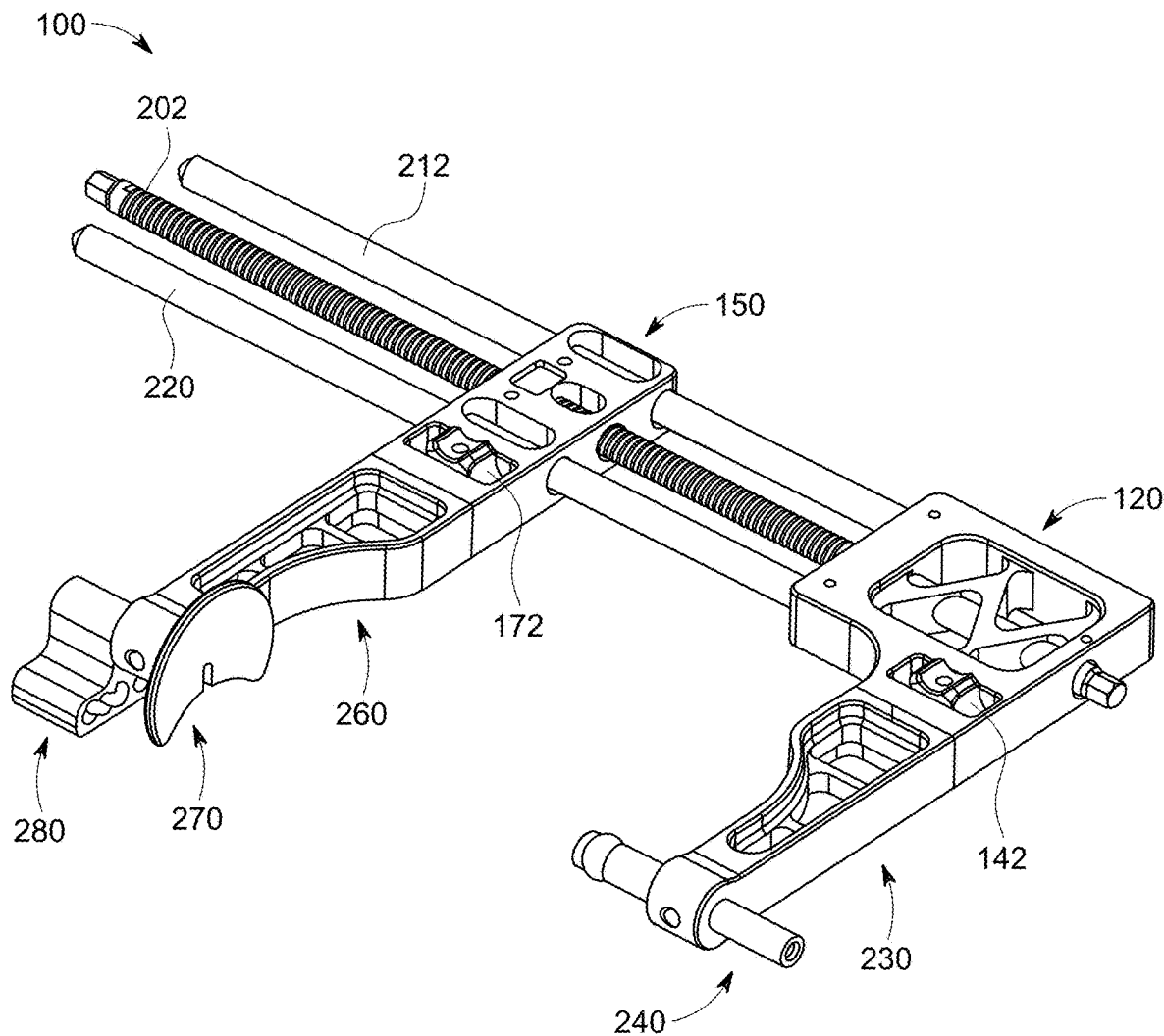
FIG. 4 is a second perspective view of the joint compression device of FIG. 3, in accordance with an aspect of the present disclosure.
Figure 5:
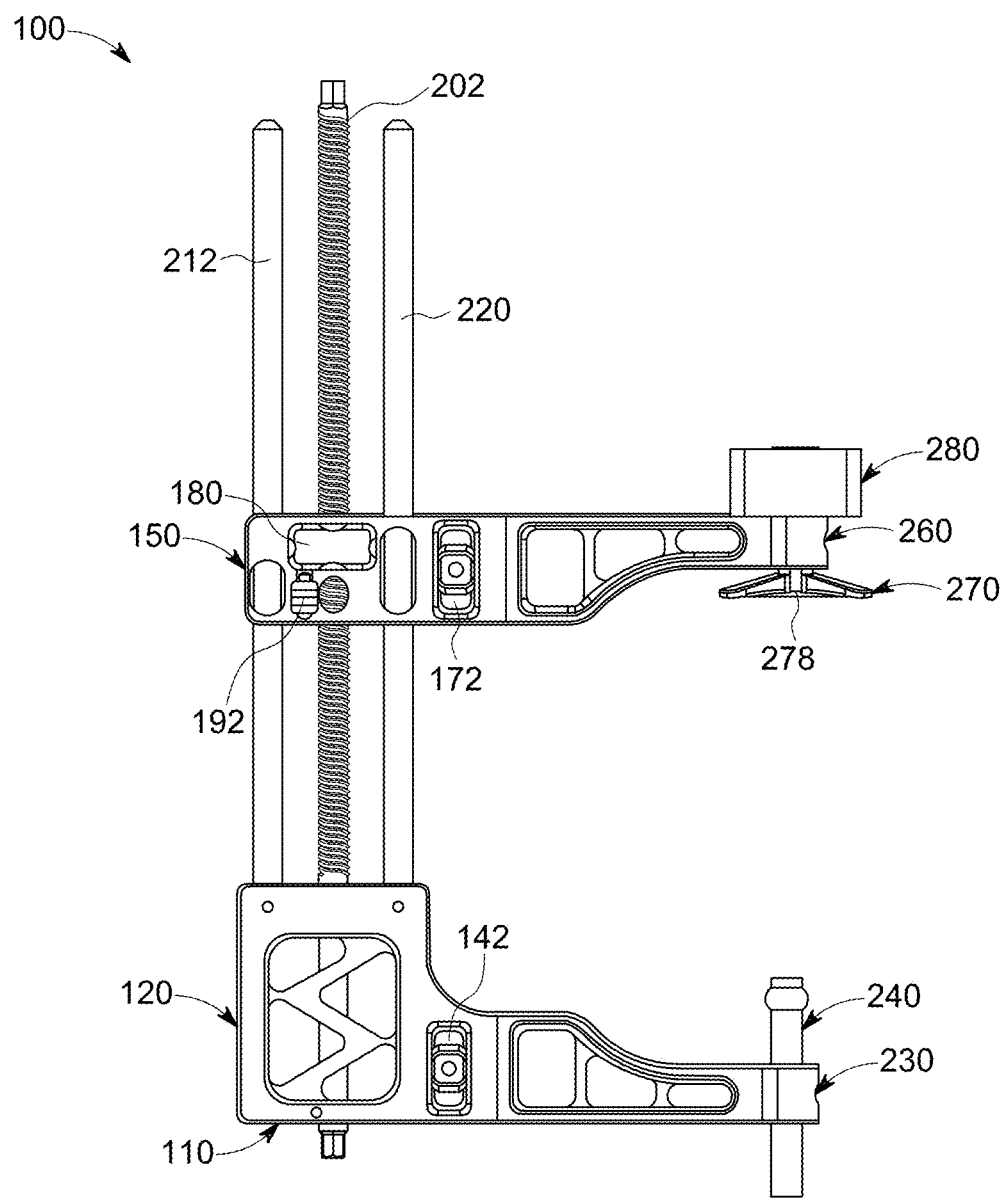
FIG. 5 is a top view of the joint compression device of FIG. 3, in accordance with an aspect of the present disclosure.
Figure 6:
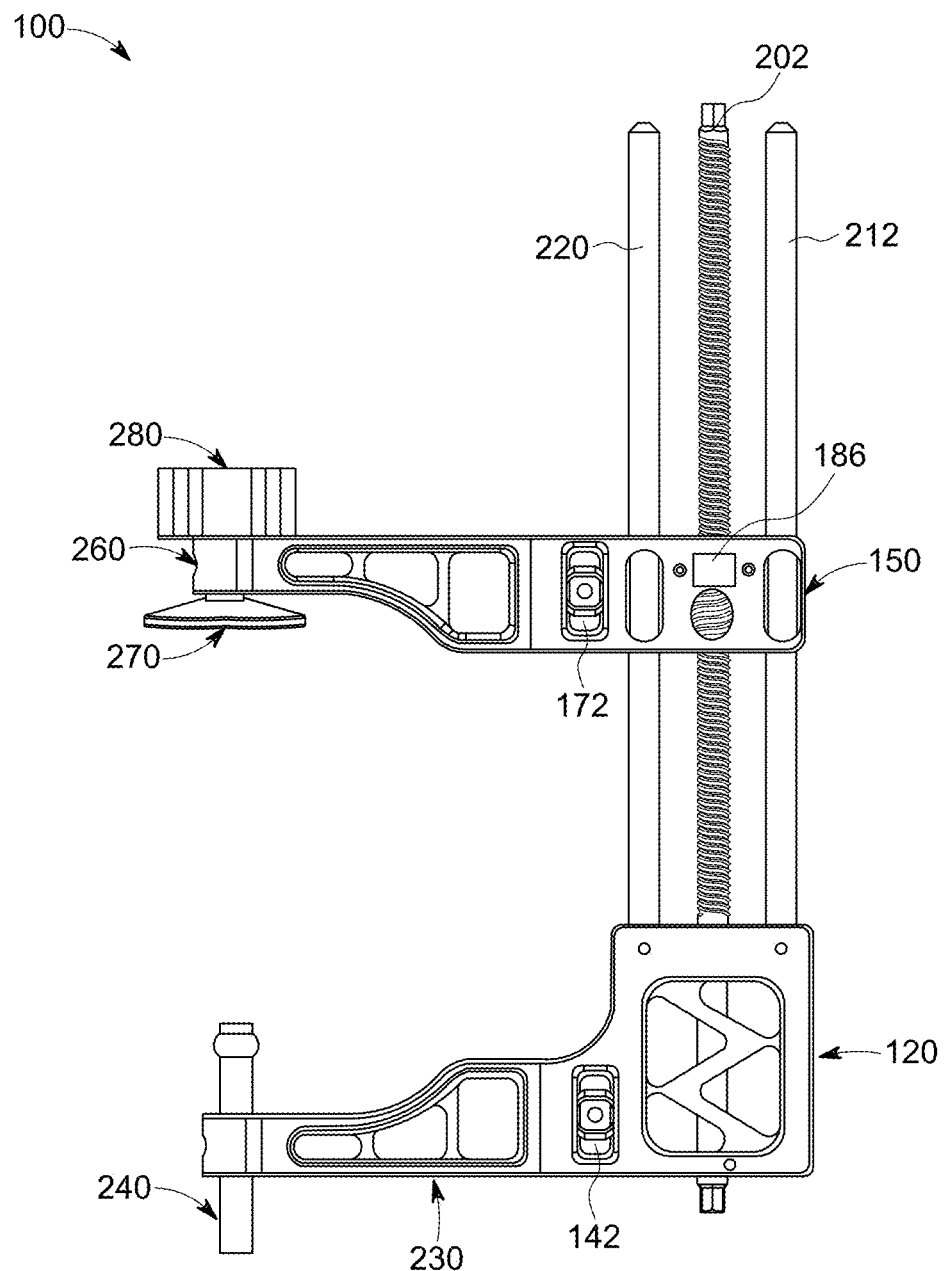
FIG. 6 is a bottom view of the joint compression device of FIG. 3, in accordance with an aspect of the present disclosure.
Figures 7, 8:
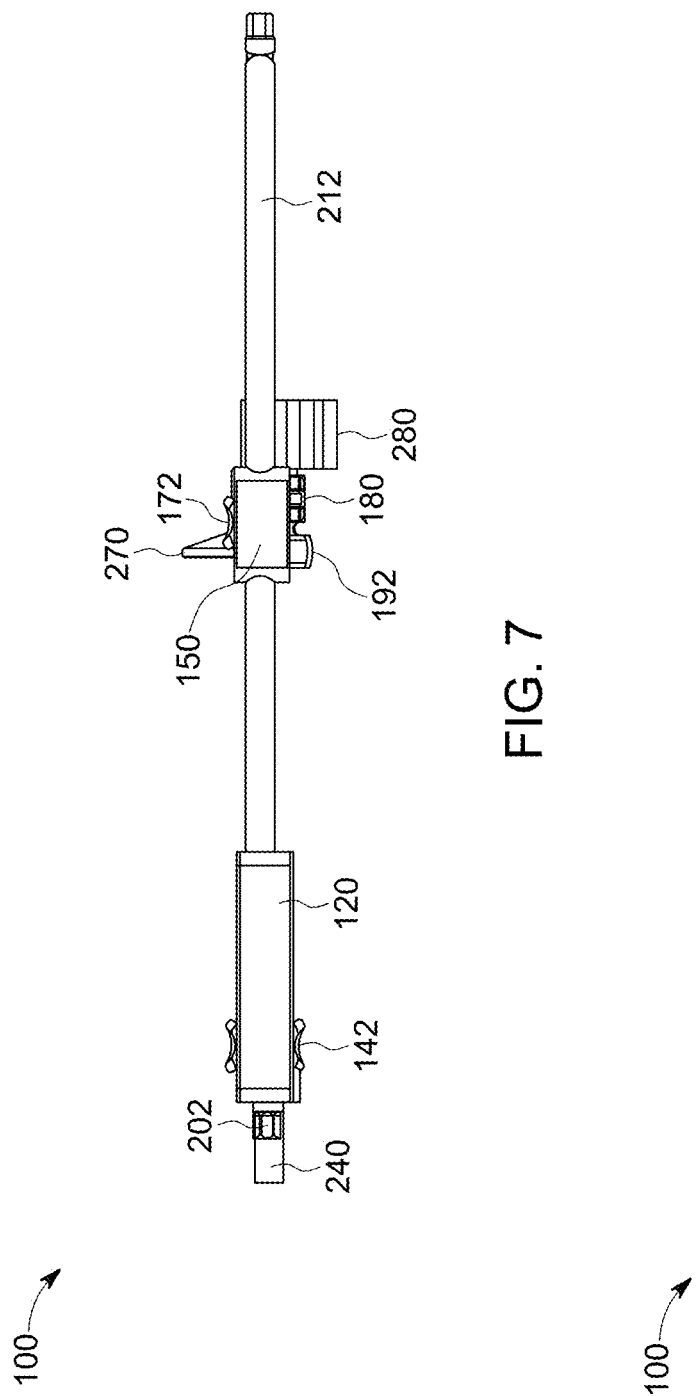
FIG. 7 is a first side view of the joint compression device of FIG. 3, in accordance with an aspect of the present disclosure.
FIG. 8 is a second side view of the joint compression device of FIG. 3, in accordance with an aspect of the present disclosure.
Figure 9:
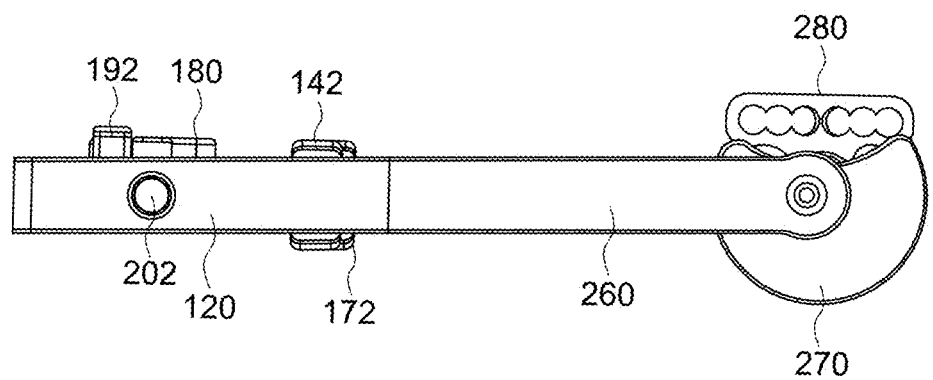
FIG. 9 is a first end view of the joint compression device of FIG. 3, in accordance with an aspect of the present disclosure.
Figure 10:
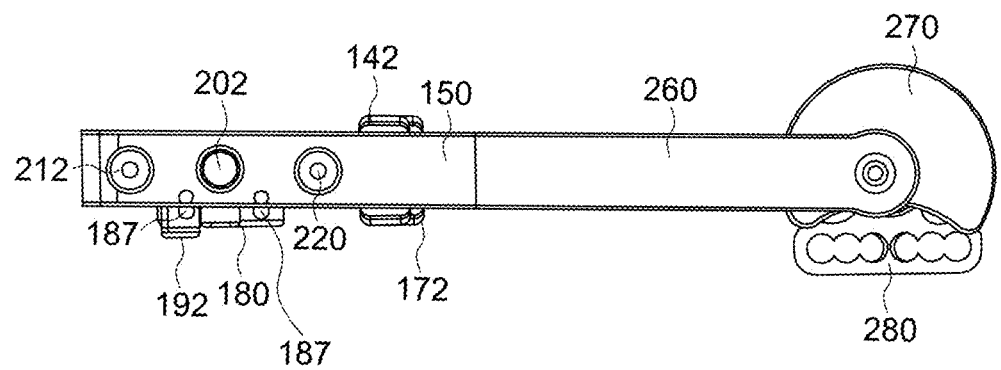
FIG. 10 is a second end view of the joint compression device of FIG. 3, in accordance with an aspect of the present disclosure.
Figure 11:
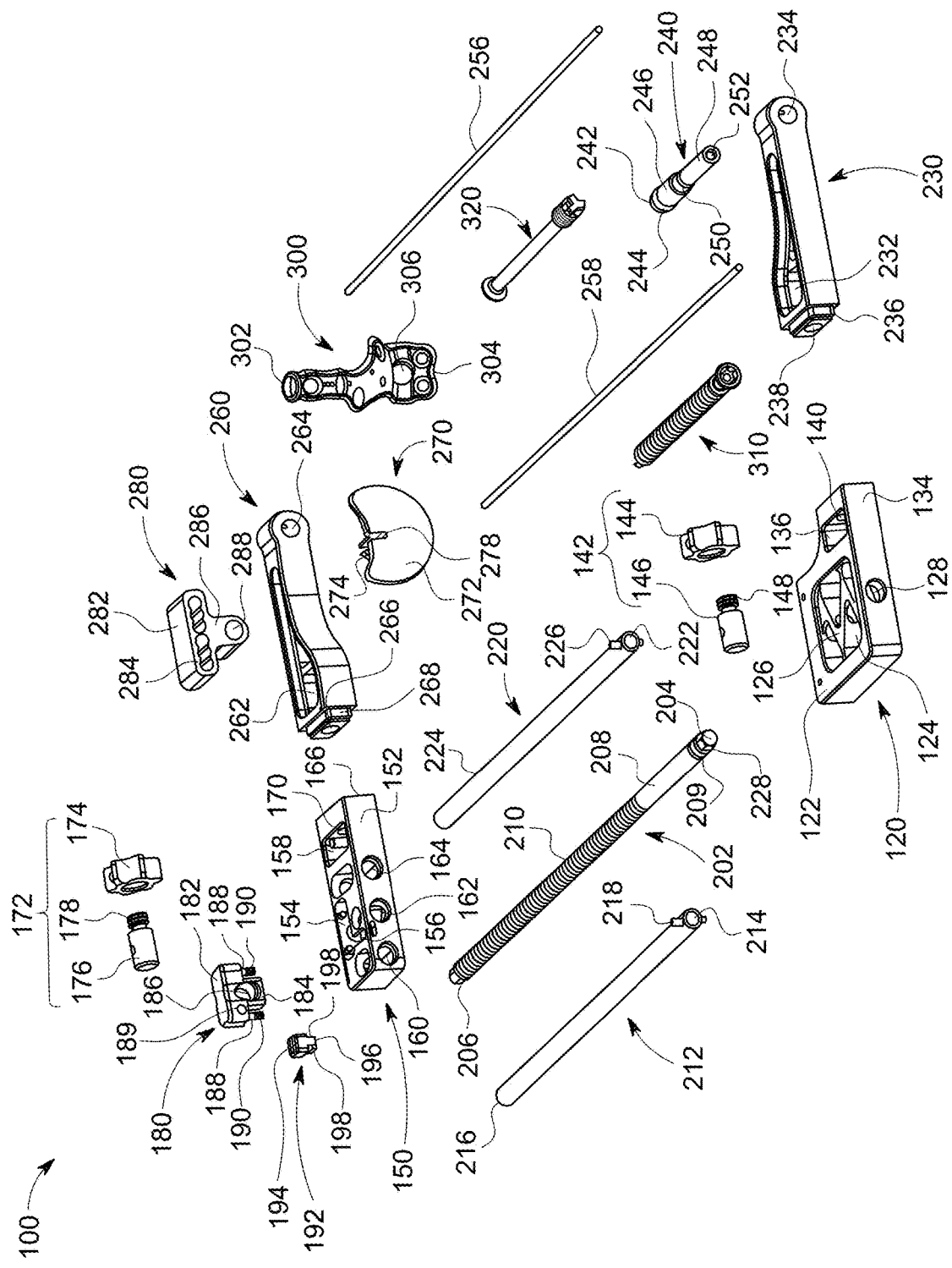
FIG. 11 is an exploded, first perspective view of the joint compression device of FIG. 3, in accordance with an aspect of the present disclosure.
Figure 12:
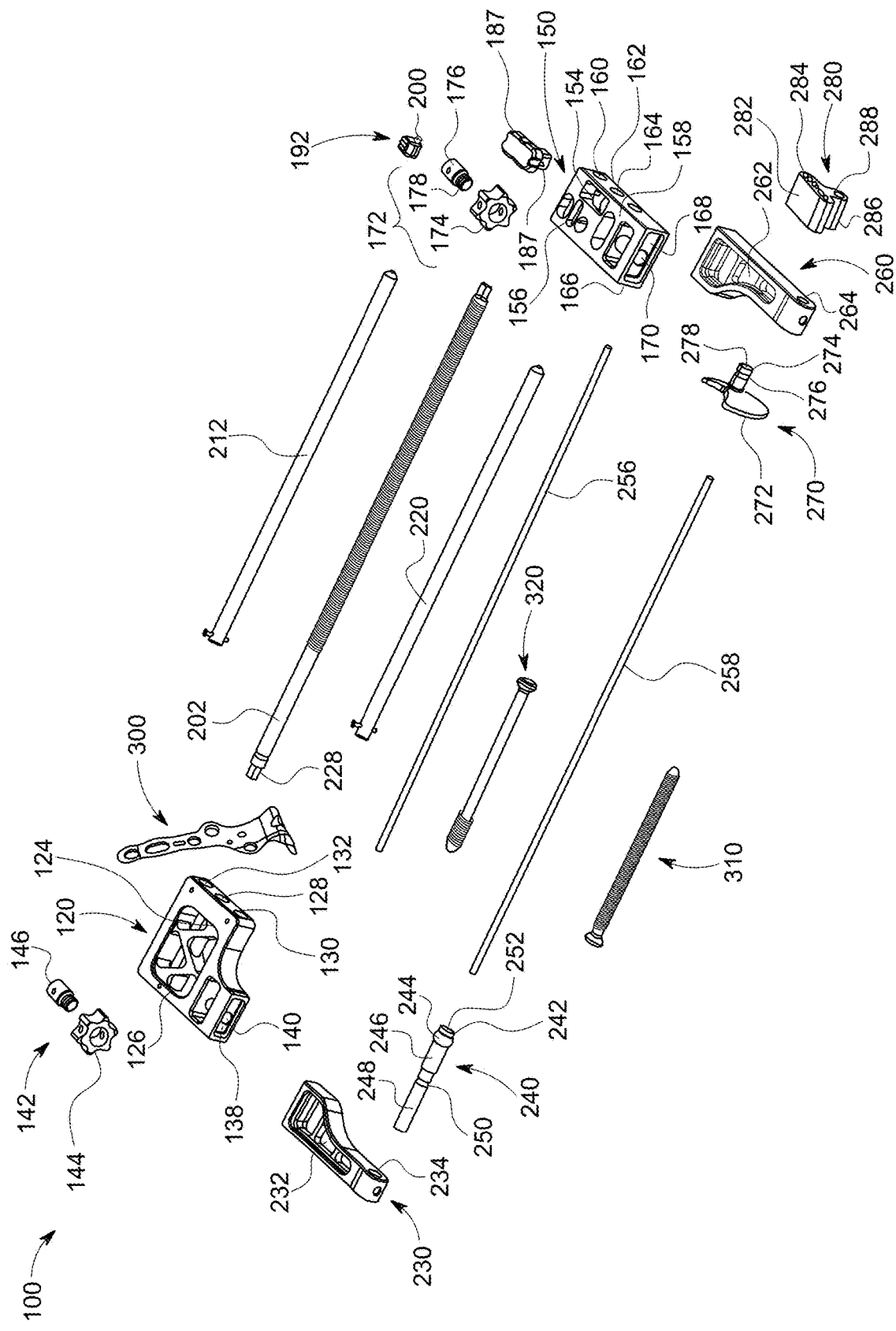
FIG. 12 is an exploded, second perspective view of the joint compression device of FIG. 3, in accordance with an aspect of the present disclosure.

Referring now to FIGS. 1-12, the first member 120 includes a body 122 with a foot member 134 extending away from the body 122 on one side of the first member 120. The body 122 may have, for example, a rectangular shape or similar polyhedron shape. The first member 120 also includes an opening 124 extending through the body 122 from a top surface to a bottom surface. The opening 124 may include, for example, at least one support member 126 extending across the opening 124. As shown, the at least one support member 126 includes three support members, although alternative numbers of support members 126 are also contemplated. The first member 120 also includes a through hole 128 extending through the body 122 from the distal end or first end to the proximal end or second end. The through hole 128 may, for example, extend through at least a portion of the at least one support member 126 as the through hole 128 extends across the opening 124. The through hole 128 may extend through the body 122 perpendicular to the opening 124. The first member 120 also includes a first hole 130 and a second hole 132, as shown in FIGS. 1, 3 and 12. The first hole 130 may be positioned on a first side of the through hole 128 and the second hole 132 may be positioned on a second side of the through hole 128. The holes 130, 132 may each be positioned adjacent to the through hole 128. Each of the holes 130, 132 may extend into the proximal end of the body 122. In the depicted embodiment, the holes 130, 132 are, for example, dead end holes that do not extend into the opening 124, although it is contemplated that the holes 130, 132 could extend into the opening 124 in alternative embodiments.

With continued reference to FIGS. 1-12, the foot member 134 may include a knob opening 136 extending through the foot member 134 from a top surface to a bottom surface. The knob opening 136 may extend through the first member 120 adjacent to the opening 124 in the body 122. The foot member 134 may also include a recessed region 138 extending into the foot member 134 on a side opposite the side of the foot member 134 coupled to the body 122, as shown in FIG. 12. The recessed region 138 may extend from the exterior surface of the foot member 134 into the foot member 134 and toward the knob opening 136. The foot member 134 further includes a third hole 140 extending from an exterior surface of the foot member 134 through the recessed region 138 and into the side of the body 122. As shown in FIGS. 11 and 12, the first member 120 may also include an attachment member 142 received within the foot member 134. The attachment member 142 may include a knob 144 and a shaft 146 that extends through an opening in the knob 144. The shaft 146 may be, for example, coupled to the knob 144 with a pin, fastener, or the like (not shown). The shaft 146 may also include a threaded portion 148 on a second end. The knob 144 is received within the knob opening 136, as shown in FIGS. 1-6. The shaft 146 extends through the third hole 140 and the first end of the shaft 146 engages the body 122 leaving the threaded portion 148 extending out of or protruding from the third hole 140 into the recessed region 138. The threaded portion 148 may be positioned to engage additional components of the joint compression device 100, as discussed in greater detail below.

The second member 150 may include a body 152 with a first opening 154 extending through the body 152 from a top surface to a bottom surface and a channel 156 extending away from a portion of the first opening 154 and into the body 152, as shown in FIGS. 11 and 12. The first opening 154 may have, for example, a first upper portion and a second lower portion, the first upper portion may be larger than the second lower portion. For example, the first upper portion may correspond to the size and shape of a base portion 182 of the button 180 and the second lower portion may correspond to the size and shape of a protrusion 184 of the button 180. The body 152 may also include a second opening 158 extending through the body 152 from the top surface to the bottom surface. The second opening 158 may be, for example, positioned near a first side and the first opening 154 and the channel 156 may be, for example, between the first side and the second side. The body 152 may further include a first through hole 160, a second through hole 162, and a third through hole 164. The holes 160, 162, 164 may extend through the body 152 from a first end to a second end. The first through hole 160 may be, for example, positioned near the second side of the body 152. The second through hole 162 may be positioned, for example, between the first through hole 160 and the second through hole 162 and to intersect the first opening 154. The third through hole 164 may be positioned between the first opening 154 and the second opening 158. The through holes 160, 162, 164 may extend through the body 152 parallel to each other as the through holes 160, 162, 164 extend from the first end to the second end.

With reference to FIG. 12, the second member 150 may also include an engagement end 166. The engagement end 166 may include a recessed region 168 extending into the body 152 from the exterior surface of the side. The engagement end 166 may also include a hole 170 extending from an exterior surface of the body 152 through the recessed region 168 and into the side of the body 152. As shown in FIGS. 11 and 12, the second member 150 may also include an attachment member 172 received within the second member 150. The attachment member 172 may include a knob 174 and a shaft 176 that extends through an opening in the knob 174. The shaft 176 may be, for example, coupled to the knob 174 with a pin, fastener, or the like (not shown). The shaft 176 may also include a threaded portion 178 on a second end. The knob 174 is received within the knob opening 176, as shown in FIGS. 1-6. The shaft 176 extends through the hole 170 and the first end of the shaft 176 engages the body 152 leaving the threaded portion 178 extending out of or protruding from the hole 170 into the recessed region 168. The threaded portion 178 may be positioned to engage additional components of the joint compression device 100, as discussed in greater detail below.

The second member 150 may also include a button 180 received within the first opening 154 and a lock or engagement lock switch 192 received within the channel 156, as shown in FIGS. 1-6. The button 180 may include a base portion 182 and a protrusion 184 extending away from a bottom surface of the base portion 182. The base portion 182 may have, for example, a shape to correspond to the shape of the upper portion of the first opening 154. The base portion 182 may also include pegs 188 extending away from the bottom surface on each side of the protrusion 184. The pegs 188 may be, for example, configured or sized and shaped to engage springs 190 received within the opening 154 to allow for translation of the button 180. The button 180 may also include a through hole or threaded hole 186 extending through the protrusion 184. The through hole 186 may align with the through hole 162 when the button 180 is positioned within the opening 154. The button 180 may also include a locking opening 189 extending into the base portion 182 of the button 180, as shown in FIG. 11. The locking opening 189 may be positioned, for example, adjacent to the through hole 186. As shown in FIGS. 10 and 12, the button 180 may include recessed slots 187 for receiving pins (not shown).

The lock 192 may include a body portion 194 with a leg 196 extending away from a bottom surface of the body portion 194. The leg 196 may include two channels 198 extending from a first end to a second end of the protrusion 198. The channels 198 may be positioned to extend along a bottom surface of the body portion 194 and the channels 198 may be inset into the leg 196, as shown in FIG. 11. The lock 192 may also include an engagement member or protrusion 200 extending away from an end of the leg 196, as shown in FIG. 12. The engagement member 200 may be positioned on the lock 192 to engage the locking opening 189 of the button 180 to stop translation of the translating member 202, as described in greater detail below.

As shown in FIGS. 11 and 12, the translating member or lead screw 202 may have a first end 204 and a second end 206. The translating member 202 may also include a coupling portion or smooth portion 208 positioned near the first end 204 and a threaded portion 210 extending from the second end 206 toward the first end 204. The coupling portion 208 may also include a groove 209 extending around the circumference of the translating member 202. The groove 209 may be, for example, sized and shaped or configured to receive a pin or locking member to secure the first end 204 of the translating member 202 to the first member 120. Each of the first end 204 and second end 206 include a drive feature for engaging a tool to rotate the translating member 202. The drive feature may be, for example, a hex-head or other polygonal shape. As shown in FIGS. 11 and 12, the drive feature 228 at the first end 204 may be, for example, removable to allow for insertion through the first member 120 and the second member 150. The first end of the translating member 202 may be, for example, inserted through the through hole 128 of the first member 120. The second end 206 of the translating member 202 may be inserted through the second through hole 162 of the second member 150. The second end 206 may also be inserted through the through hole 186 of the button 180 to allow for the translating member 202 to be secured positioning the second member 150 at the desired separation from the first member 120.

With continued reference to FIGS. 11 and 12, the first bar 212 may include a first end 214 and a second end 216. The first end 214 may be inserted into the second hole 132 of the first member 120 and coupled to the first member 120 with a pin 218. The second end 216 may be inserted through the first through hole 160. The second bar 220 may include a first end 222 and a second end 224. The first end 222 may be inserted into the first hole 130 of the first member 120 and coupled to the first member 120 with a pin 226. The second end 224 may be inserted through the third through hole 164.

Referring now to FIGS. 1-14, the joint compression device 100 includes the base system 110, a first arm 230, and a second arm 260. The system 100 may also include a tube or plate engagement tube 240 and a k-wire guide 280. Further, the system 100 may include a plate 300, guide wires or k-wires 256, 258, a first fastener 310, and a second fastener 320, as shown in FIGS. 11 and 12. The first arm 230 includes an opening or window 232 extending through the first arm 230 from a top surface to a bottom surface. The first arm 230 also includes a through hole 234 extending through a second end of the first arm 230 from a first end to a second end. The through hole 234 may extend through the first arm 230 perpendicular to the opening 232. The first arm 230 may also include a protrusion 236 extending away from a first end of the first arm 230. The protrusion 236 may be, for example, sized and shaped to be received within the recessed region 138 of the first member 120. The first arm 230 may further include a coupling opening or threaded opening 238 extending from an exterior surface through the protrusion 236. The coupling opening 238 may be, for example, sized and shaped to receive the threaded portion 148 of the attachment member 142. The plate engagement tube or tube 240 may include an engagement end 242 for contacting a bone plate, for example, bone plate 300. The tube 240 may also include a hole engagement member 244 for engaging a corresponding hole 306 in the bone plate 300. The tube 240 may further include a stop member 246 to prevent the tube 240 from passing entirely through the through hole 234. The tube 240 may also include a shaft portion 248 for insertion into the through hole 234 and a groove 250 extending around the shaft portion 248. The tube 240 may be secured to the first arm 230 by a pin (not shown) inserted into the first arm 230 and engaging the groove 250 in the tube 240. In addition, the tube 240 may include a through hole 252 extending along the longitudinal axis of the tube 240. The through hole 252 may be, for example, configured or sized and shaped to receive a k-wire or guide wire 256.

With continued reference to FIGS. 11 and 12. The second arm 260 includes an opening or window 262 extending through the second arm 260 from a top surface to a bottom surface. The second arm 260 also includes a through hole 264 extending through a second end of the second arm 260 from a first end to a second end. The through hole 264 may extend through the second arm 260 perpendicular to the opening 262. The second arm 260 may also include a protrusion 266 extending away from a first end of the second arm 260. The protrusion 266 may be, for example, sized and shaped to be received within the recessed region 168 of the second member 150. The second arm 260 may further include a coupling opening or threaded opening 268 extending from an exterior surface through the protrusion 266. The coupling opening 268 may be, for example, sized and shaped to receive the threaded portion 178 of the attachment member 172. The foot engagement member or heel pad 270 may be, for example, received within the through hole 264 of the second arm 260. The foot engagement member 270 may include a base 272 sized and shaped or configured to receive a portion of a patient's heel. The base 272 may be, for example, semi-circular shaped and curved to form a concave surface for contacting or receiving a patient's heel. The engagement member 270 may also include a shaft 274 extending away from a bottom surface of the base 272. The shaft 274 includes a groove 276 extending circumferentially around the shaft 274 for receiving a coupling member, such as a pin to secure the engagement member 270 to the second arm 260. The base 272 and shaft 274 may each include a channel 278 recessed into the base 272 and shaft 274 from an exterior surface, as shown in FIGS. 11 and 12. The channel 278 may extend along the longitudinal axis of the engagement member 270. The optional k-wire guide 280 may be positioned to align with the through hole 264 of the second arm 260. The k-wire guide 280 may include a body portion 282 and a leg or extension member 286 extending away from a bottom surface of the body portion 282. The k-wire guide 280 may have, for example, a T-shape. The body portion 282 may include a plurality of holes 284 extending through the guide 280 from a first end to a second end. The holes 284 may be, for example, separate holes, overlapping holes, or a combination of separate overlapping holes. The extension member 286 may also include a through hole 288 extending through the guide 280 from a first end to a second end. The through hole 288 may be aligned with the through hole 264 of the second arm 260 to receive the guide wire 256. Once the guide wire 256 is positioned within the through hole 288, the guide 280 may be used for insertion of a second guide wire 258 through one of the plurality of holes 284 and into the patient's foot.

Once assembled, as shown in FIGS. 1-6, the first joint compression device 100 allows for the second member 150 to slide over the screw 202 and bars 212, 220 and to translate along the path of the screw 202 and bars 212, 220. The button 180 of the second member 150 may be depressed to disengage the threads 210 of the screw 202 and allow for rapid translation along the parallel screw 202 and bars 212, 220. When the button 180 is released, the button 180 engages the threads 210 of the screw 202. The engaged button 180 may be locked into place by engaging the engagement member 200 of the engagement lock 192, as shown in FIG. 12, with the locking opening 189 of the button 180, as shown in FIG. 11. The second member 150 translates along the screw 202 and bars 212, 220 independent of the first member 120. With continued reference to FIGS. 1-6, the screw 202 of the first member 120 may be rotated to allow the second member 150 to translate back and forth with respect to the first member 120. The attachment members 142, 172 of the first and second members 120, 150 allow for attachment of interchangeable arms for various procedures, as discussed in greater detail below.

Figure 13:
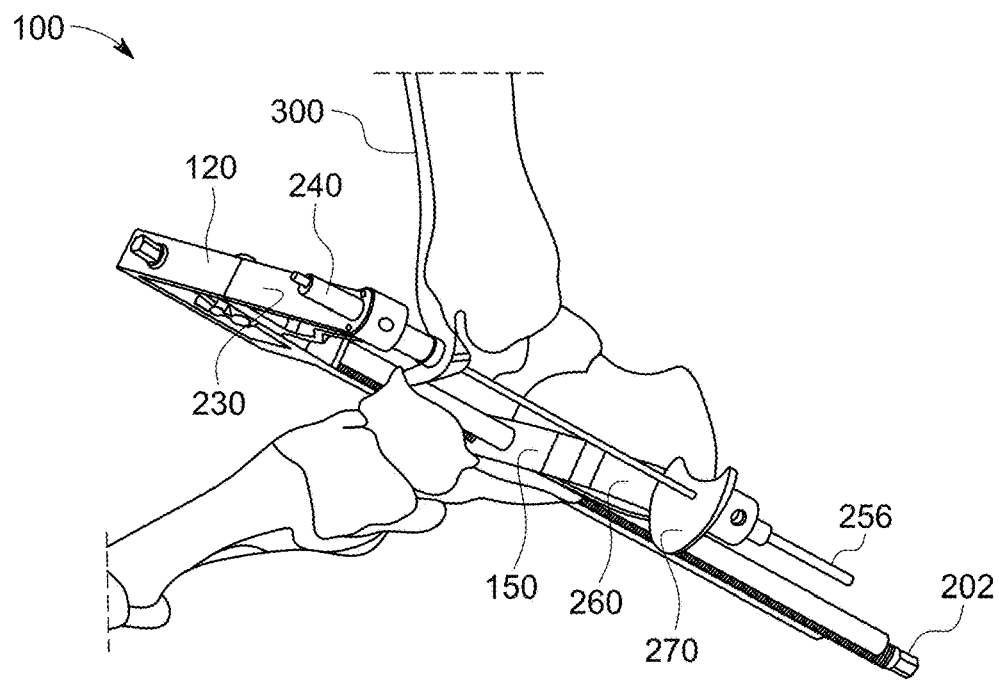
FIG. 13 is a side perspective view of the joint compression device of FIG. 3 positioned on a foot, in accordance with an aspect of the present disclosure.
Figure 14:
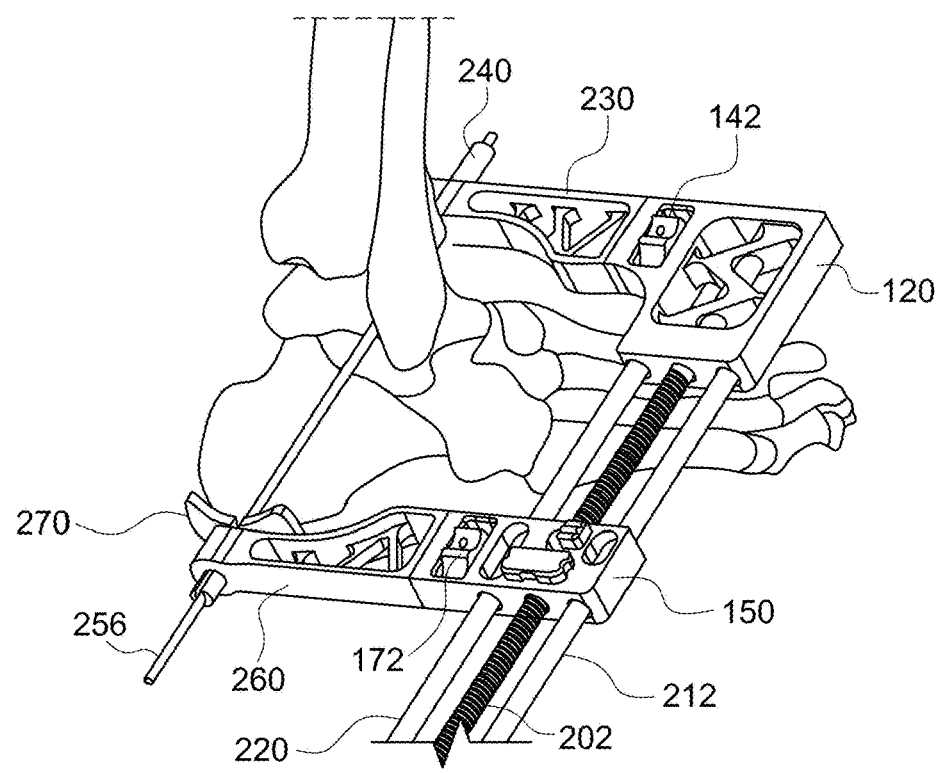
FIG. 14 is a rear perspective view of the joint compression device and the foot of FIG. 13, in accordance with an aspect of the present disclosure.
Figure 15:
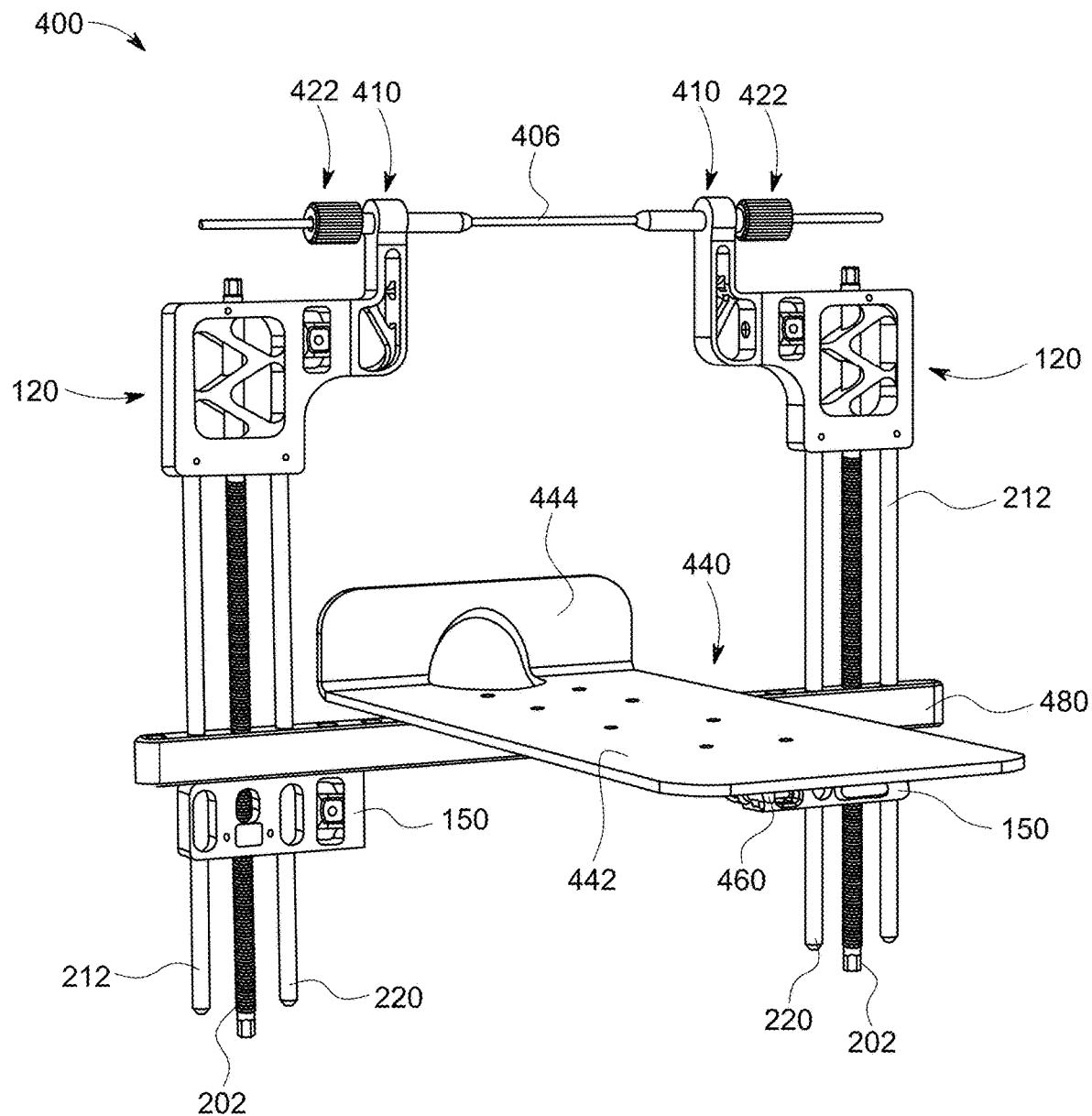
FIG. 15 is a first perspective view of another joint compression device, in accordance with an aspect of the present disclosure.
Figure 16:
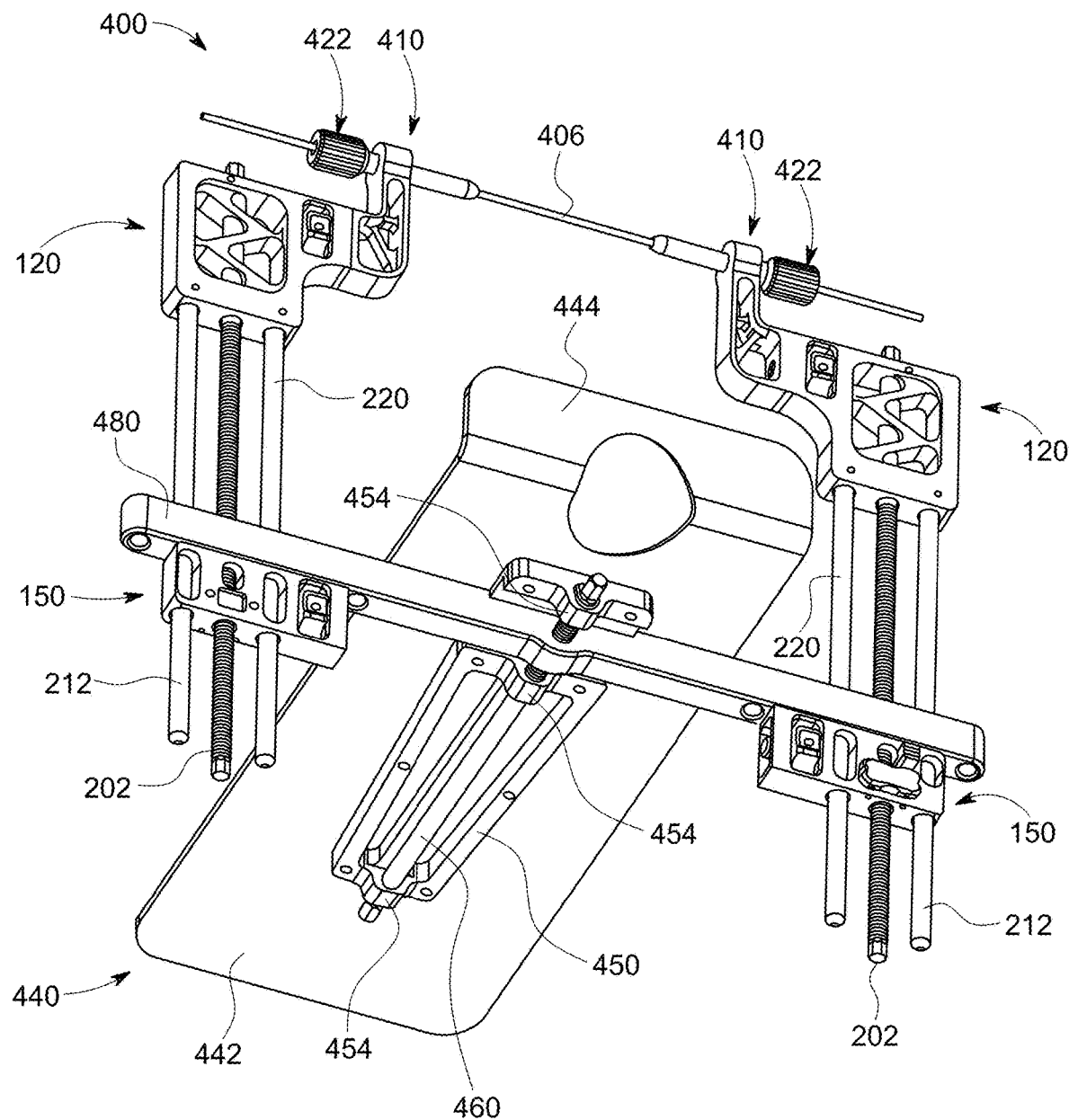
FIG. 16 is a second perspective view of the joint compression device of FIG. 15, in accordance with an aspect of the present disclosure.
Figure 17:
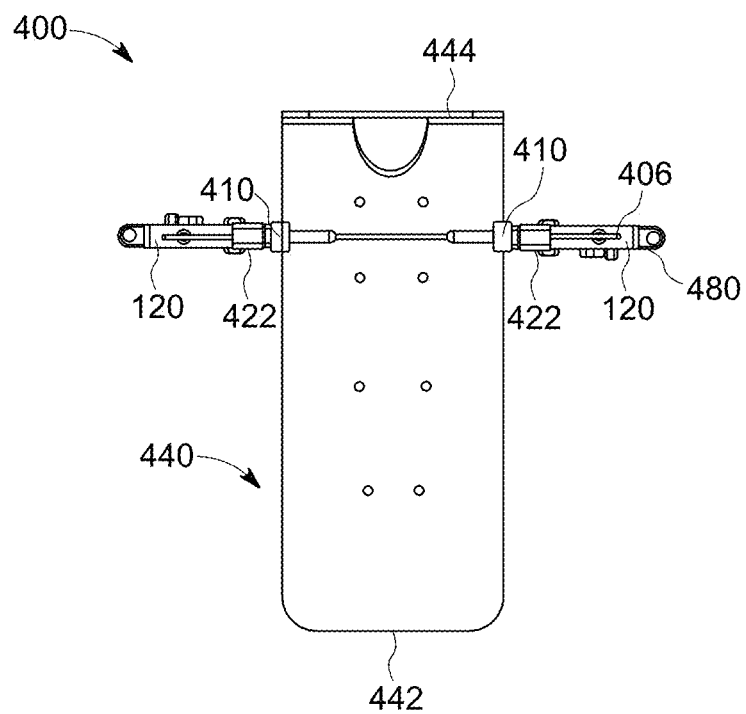
FIG. 17 is a top view of the joint compression device of FIG. 15, in accordance with an aspect of the present disclosure.

With reference to the first joint compression device 100 the base system 110 may be used with the arms 230, 260 to implant an anterior tibiotalocalcaneal (TTC) fusion plate. For implantation the arms 230, 260 are coupled to the first member 120 and second member 150, respectively, using the attachment members 142, 172. The tube 240 is then mated with the plate 300 and the foot engagement member 270 is placed on the desired target on the back of a patient's heel, as shown in FIGS. 13 and 14. A guide wire 256 is then inserted through the tube 240 and across the patient's bones and through the foot engagement member 270. Once the guide wire 256 is in place, the screw 202 may be rotated to compress the subtalar joint.

Figure 23:
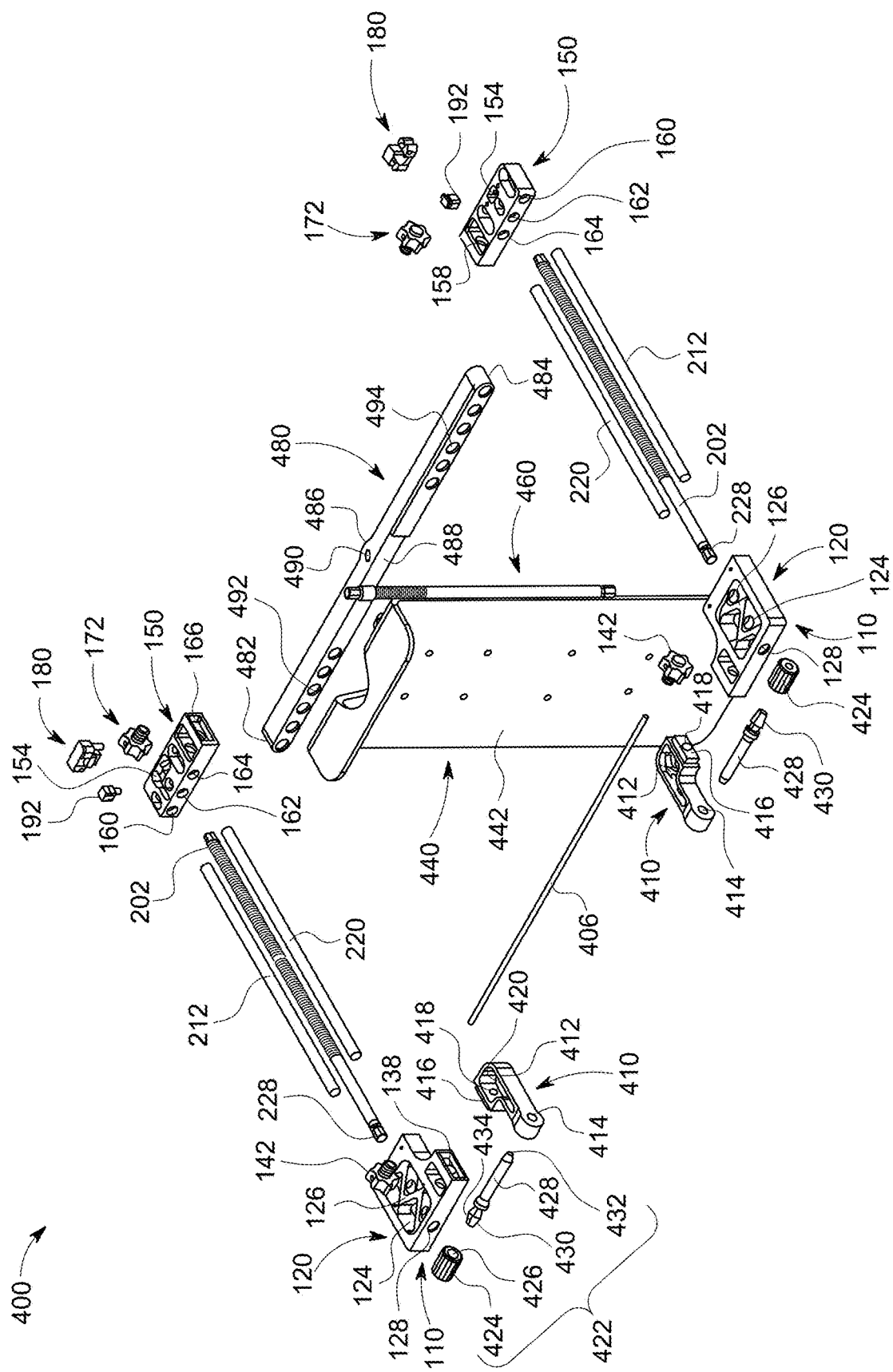
FIG. 23 is an exploded, first perspective view of the joint compression device of FIG. 15, in accordance with an aspect of the present disclosure.
Figure 24:
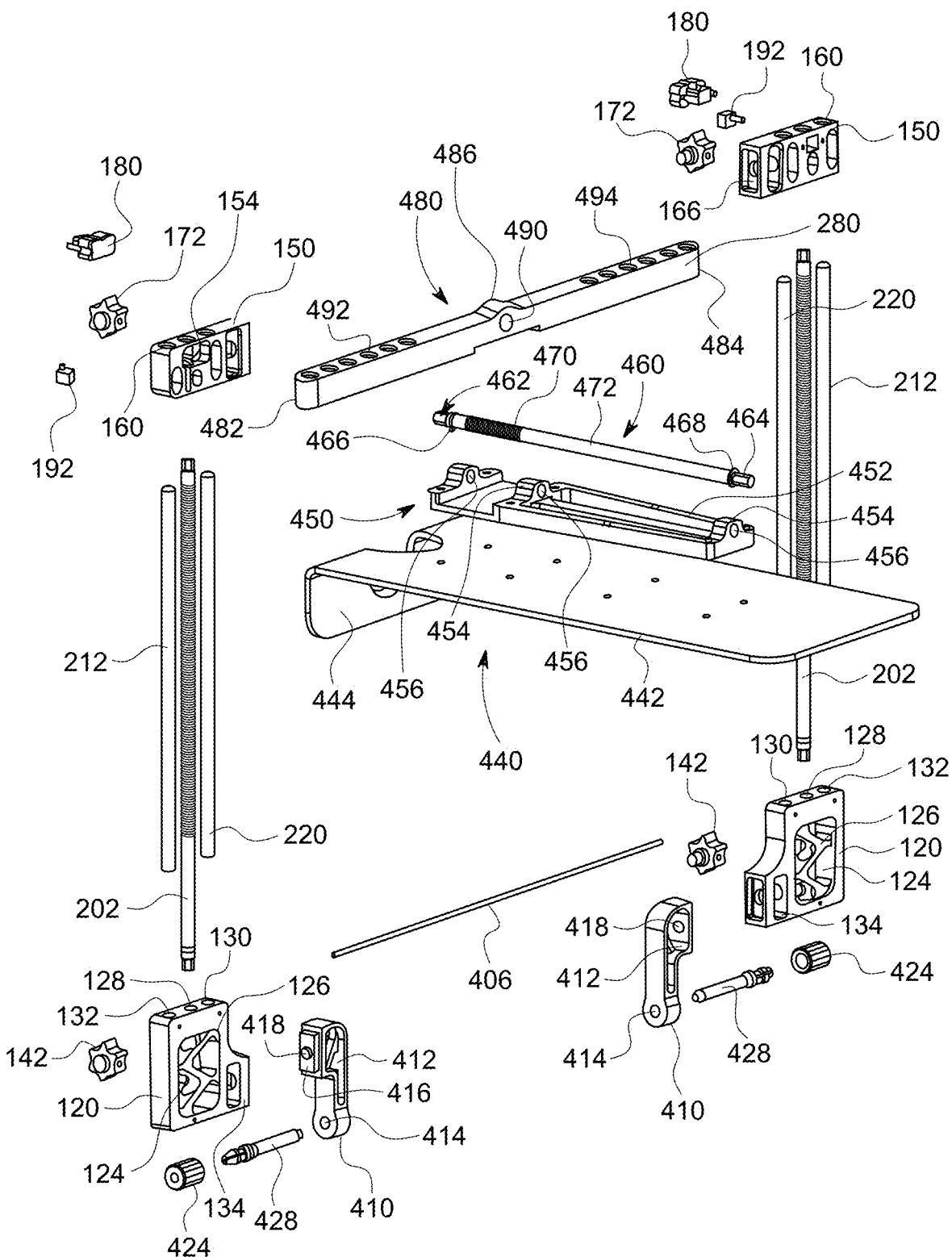
FIG. 24 is an exploded, second perspective view of the joint compression device of FIG. 15, in accordance with an aspect of the present disclosure.

Referring now to FIGS. 15-27 and more specifically FIGS. 23 and 24, the second joint compression device 400 includes a first base system 110, a first arm 410, a second base system 110, a second arm 410, and a foot plate assembly 440. The second joint compression device 400 may also include a first k-wire guide tube 422, a second k-wire guide tube 422, and a guide wire or k-wire 406. The arms 410 may be, for example, "L" shaped. The arms 410 may include openings or windows 412 extending through the arms 410 from a top surface to a bottom surface. The arms 410 also include through holes 414 extending through the second ends of the arms 410 from a first end to a second end. The through holes 414 may extend through the arms 410 perpendicular to the openings 412. The arms 410 may also include protrusions 416 extending away from the first ends of the arms 410. The protrusions 416 may be, for example, sized and shaped to be received within the recessed regions 138 of the first members 120. The arms 410 may further include a coupling opening or threaded opening 418 extending from the exterior surfaces through the protrusions 416. The coupling opening 418 may be, for example, sized and shaped to receive the threaded portion 148 of the attachment member 142. The arms 410 may also include support structures 420 extending across the openings 412. The k-wire guide tubes 422 may each include a knob 424 with a through hole 426 and a shaft 428 with a coupling portion 430, as shown in FIGS. 23 and 24. The coupling portion 430 is received within the through hole 426 of the knob 424. The shaft 428 and coupling portion 430 also include a through hole 432 extending through the shaft 428 and coupling portion 430 along a longitudinal axis of the guide tubes 422. The coupling portion 430 may include, for example, a plurality of deformable members 434 allowing for the members to deflect when inserted into the through hole 426 of the knob 424 and to engage a recess (not shown) within the through hole 426 of the knob 424 to secure the coupling portion 430 to the knob 424.

Figure 18:
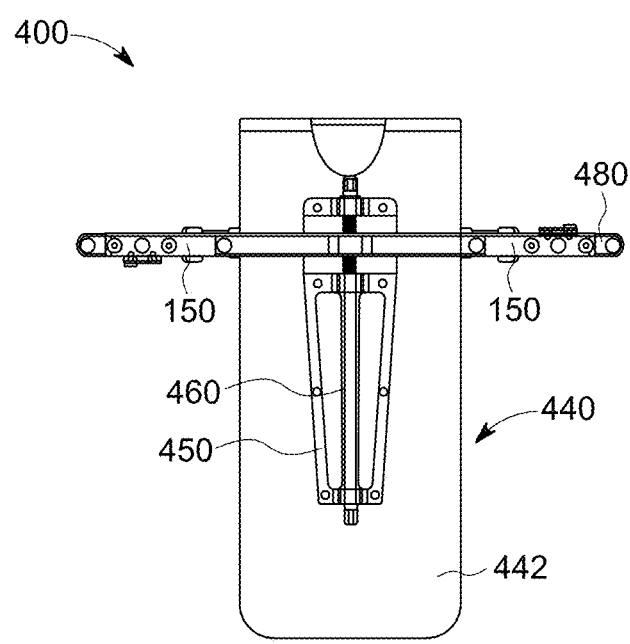
FIG. 18 is a bottom view of the joint compression device of FIG. 15, in accordance with an aspect of the present disclosure.
Figure 19:
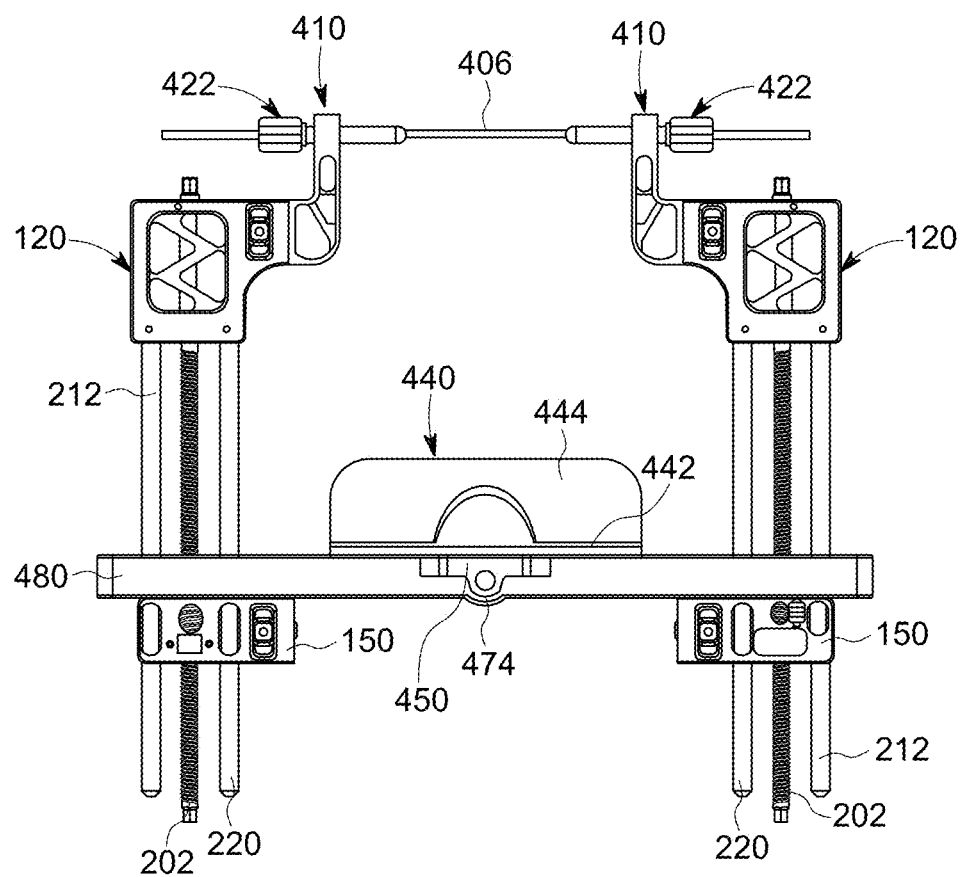
FIG. 19 is a first end view of the joint compression device of FIG. 15, in accordance with an aspect of the present disclosure.
Figure 20:
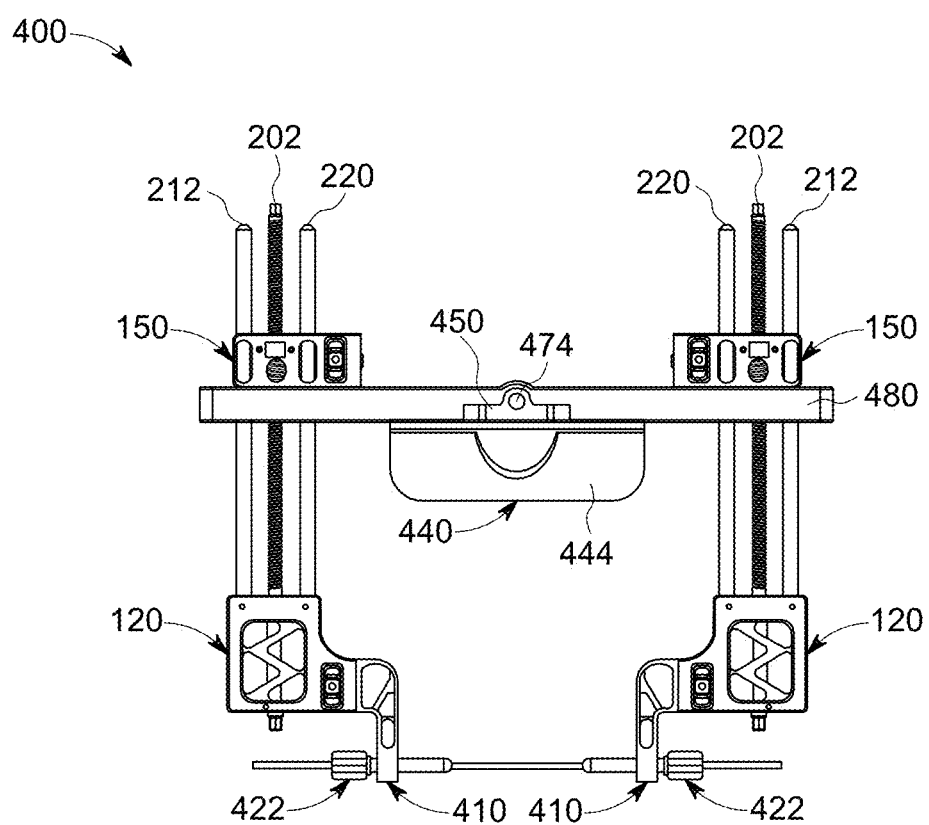
FIG. 20 is a second end view of the joint compression device of FIG. 15, in accordance with an aspect of the present disclosure.
Figure 21:
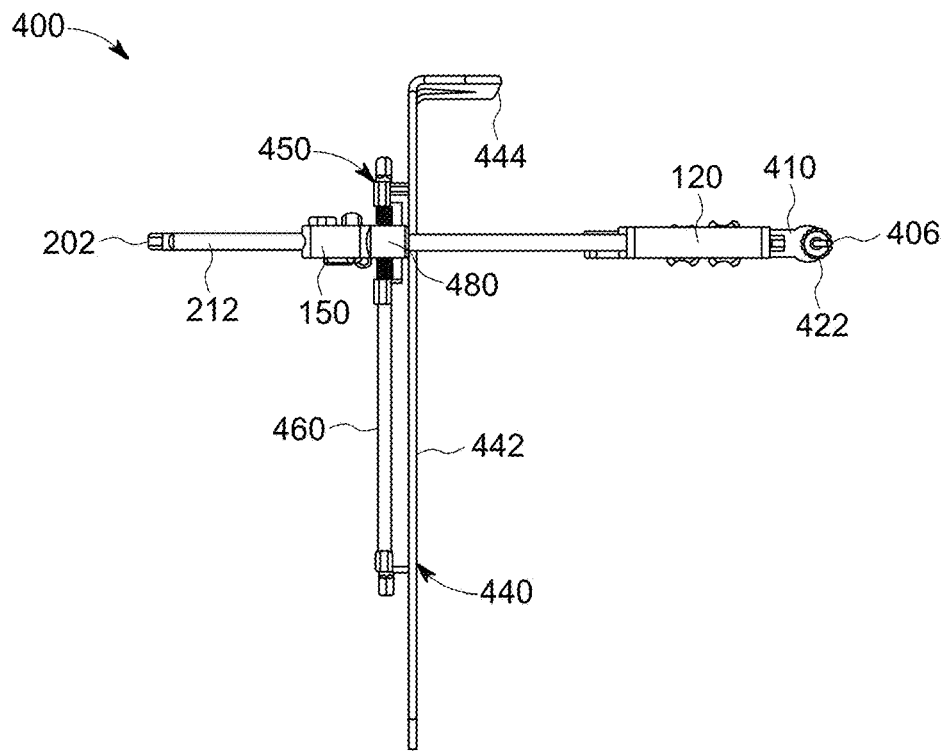
FIG. 21 is a first side view of the joint compression device of FIG. 15, in accordance with an aspect of the present disclosure.
Figure 22:
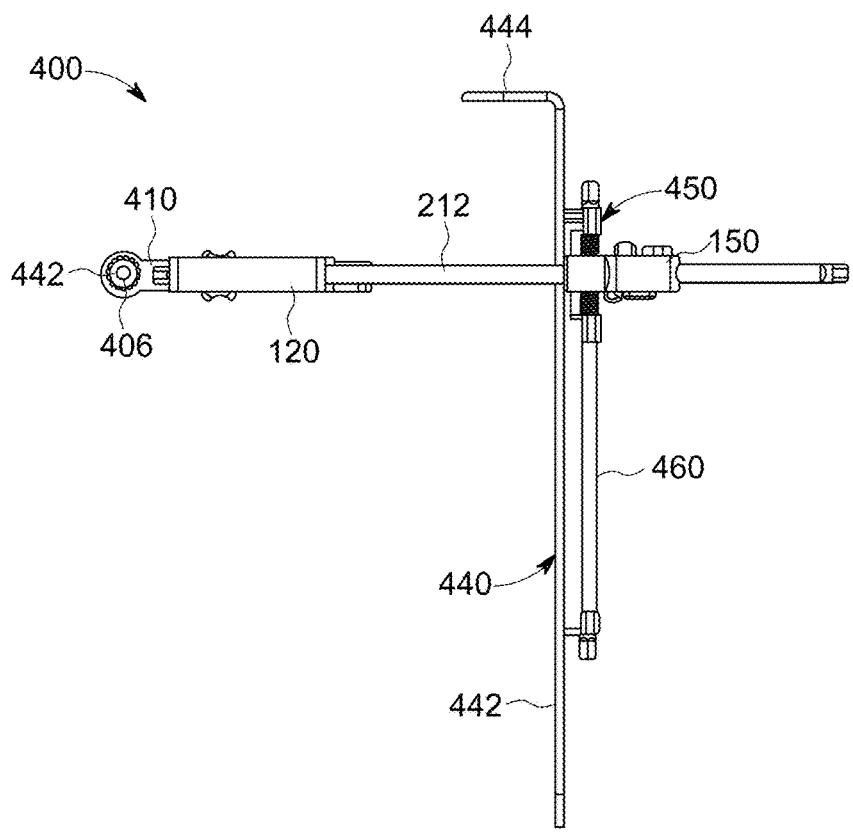
FIG. 22 is a second side view of the joint compression device of FIG. 15, in accordance with an aspect of the present disclosure.

With continued reference to FIGS. 23 and 24, the foot plate assembly 440 includes a foot plate 442, a foot plate adjustment base 450, a foot plate adjustment screw 460, and a foot plate compressor bar 480. The foot plate 442 includes an extension 444 positioned perpendicular to the foot plate 442. The foot plate adjustment base 450 is secured to a bottom surface of the foot plate 442. As shown in FIG. 24, the foot plate adjustment base 450 includes a frame 452 with protrusions 454 extending away from a bottom surface of the frame 452. The frame 452 also includes through holes 456 extending through the protrusions 454 along the longitudinal axis of the frame 452. As shown in FIG. 18, the frame 452 tapers from the first end to the second end. The through holes 456 are sized and shaped or configured to receive the foot plate adjustment screw 460. The adjustment screw 460 may include a first end 462 and a second end 464. The first end 462 may include a first groove 466 for receiving a securement clip 474, as shown in FIG. 19. The second end 464 may include a second groove 468 for receiving a securement clip 474, as shown in FIG. 20. The adjustment screw 460 may also include a threaded portion 470 and a shaft portion or smooth portion 472. The threaded portion 470 may engage a first through hole 490 on the foot plate compressor bar 480. The foot plate compressor bar 480 also includes a first end 482 and a second end 484. The compressor bar 480 also includes a raised region or protrusion 486 positioned between the first end 482 and the second end 484 of the compressor bar 480. The compressor bar 480 may also include a recessed region 488 positioned between the first end 482 and the second end 484 on a side of the compressor bar 480 opposite the protrusion 486. The compressor bar 480 also includes a plurality of second through holes 492 positioned between the first through hole 490 and the first end 482 and a plurality of third through holes 494 positioned between the first through hole 490 and the second end 484. The first through hole 490 may extend through the compressor bar 480 perpendicular to the direction that the plurality of second through holes 492 and the plurality of third through holes 494 extend through the compressor bar 480.

With reference to the second joint compression device 400 two base systems 110 may be used with the arms 410 and the foot plate assembly 440 to implant a tibiotalar (TT) fusion plate. For implantation the second joint compression device 400 may be assembled by coupling a first screw 202, a right first bar 212, and a right second bar 220 to a right first member 120 and a second screw 202, a left first bar 212, and a left second bar 220 to a left first member 120. A right arm 410 may then be coupled to the right first member 120 and a left arm 410 may be coupled to the left first member 120 using attachment members 142. The right and left guide tubes 422 may then be inserted into the right and left arms 410, respectively, and a guide wire or k-wire 406 may be inserted through the through holes 432 of the tubes 422. The first screw 202, the right first bar 212, and the right second bar 220 may be inserted through the plurality of second through holes 492 in the compressor bar 480. The second screw 202, the left first bar 212, and the left second bar 220 may be inserted through the plurality of third through holes 494 in the compressor bar 480. Once the compressor bar 480 is coupled to the screws 202 and bars 212, 220, the second members 150 may be coupled to the screws 202 and bars 220 and the second members 150 may contact the compressor bar 480. In addition, the coupled foot plate 442 and adjustment base 450 may be secured to the compressor bar 480 using the adjustment screw 460.

Figure 25:
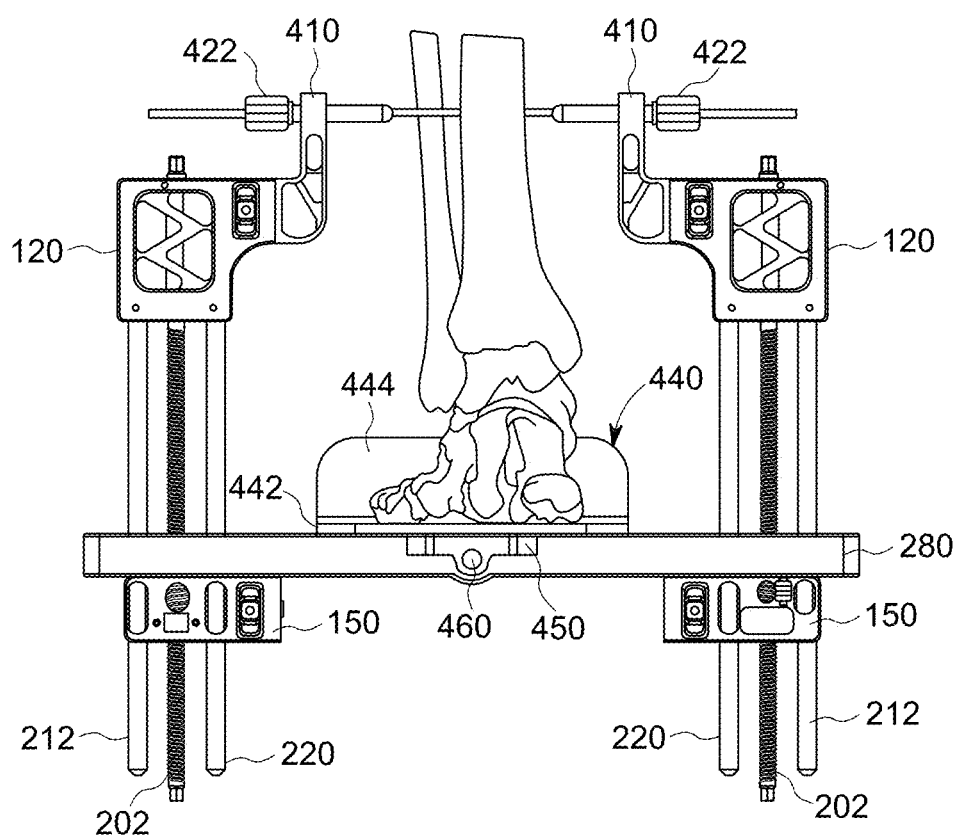
FIG. 25 is a first end view of the joint compression device of FIG. 15 coupled to a foot, in accordance with an aspect of the present disclosure.
Figure 26:
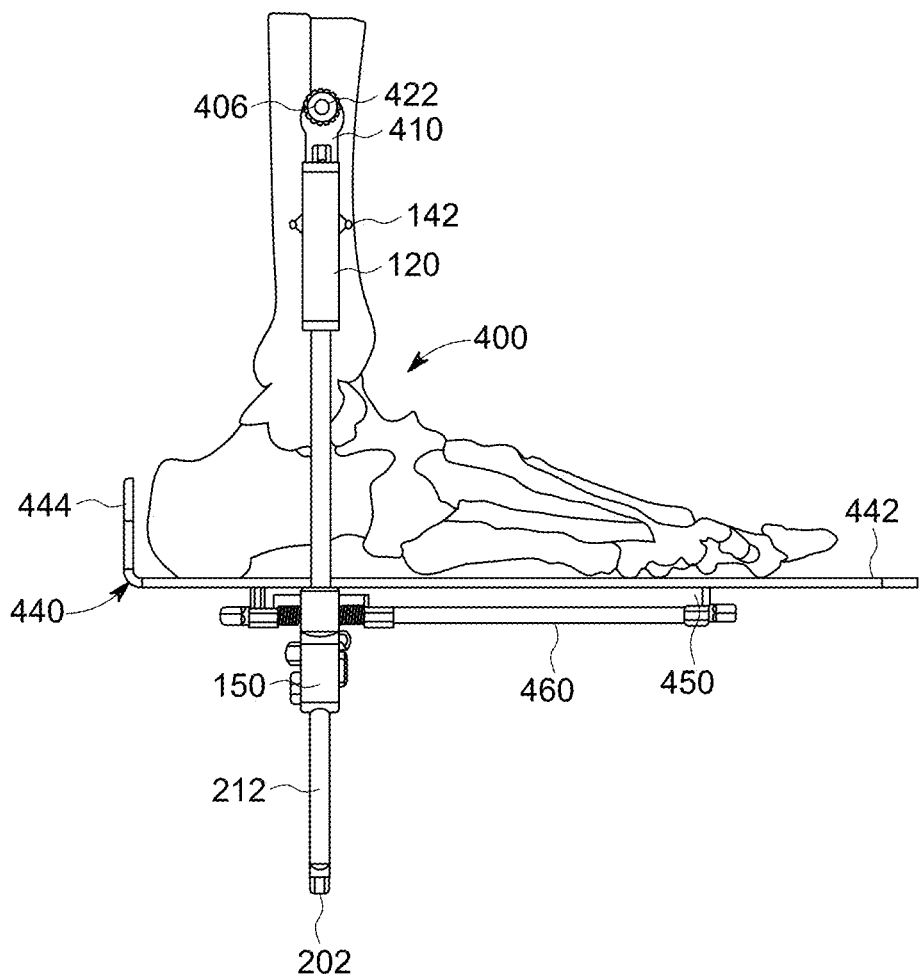
FIG. 26 is a side view of the joint compression device and foot of FIG. 25, in accordance with an aspect of the present disclosure.
Figure 27:
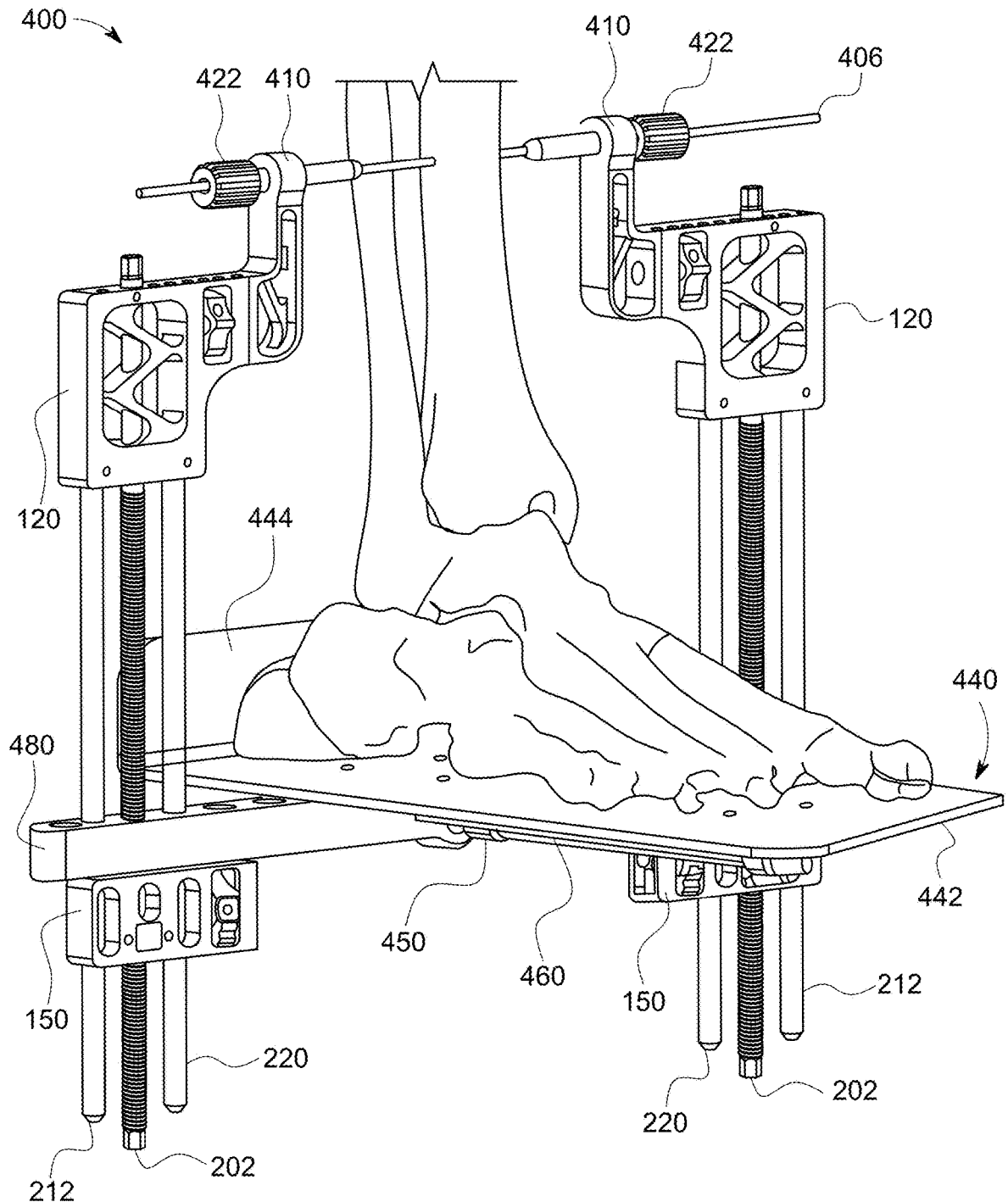
FIG. 27 is a perspective view of the joint compression device and foot of FIG. 25, in accordance with an aspect of the present disclosure.
Figure 28:
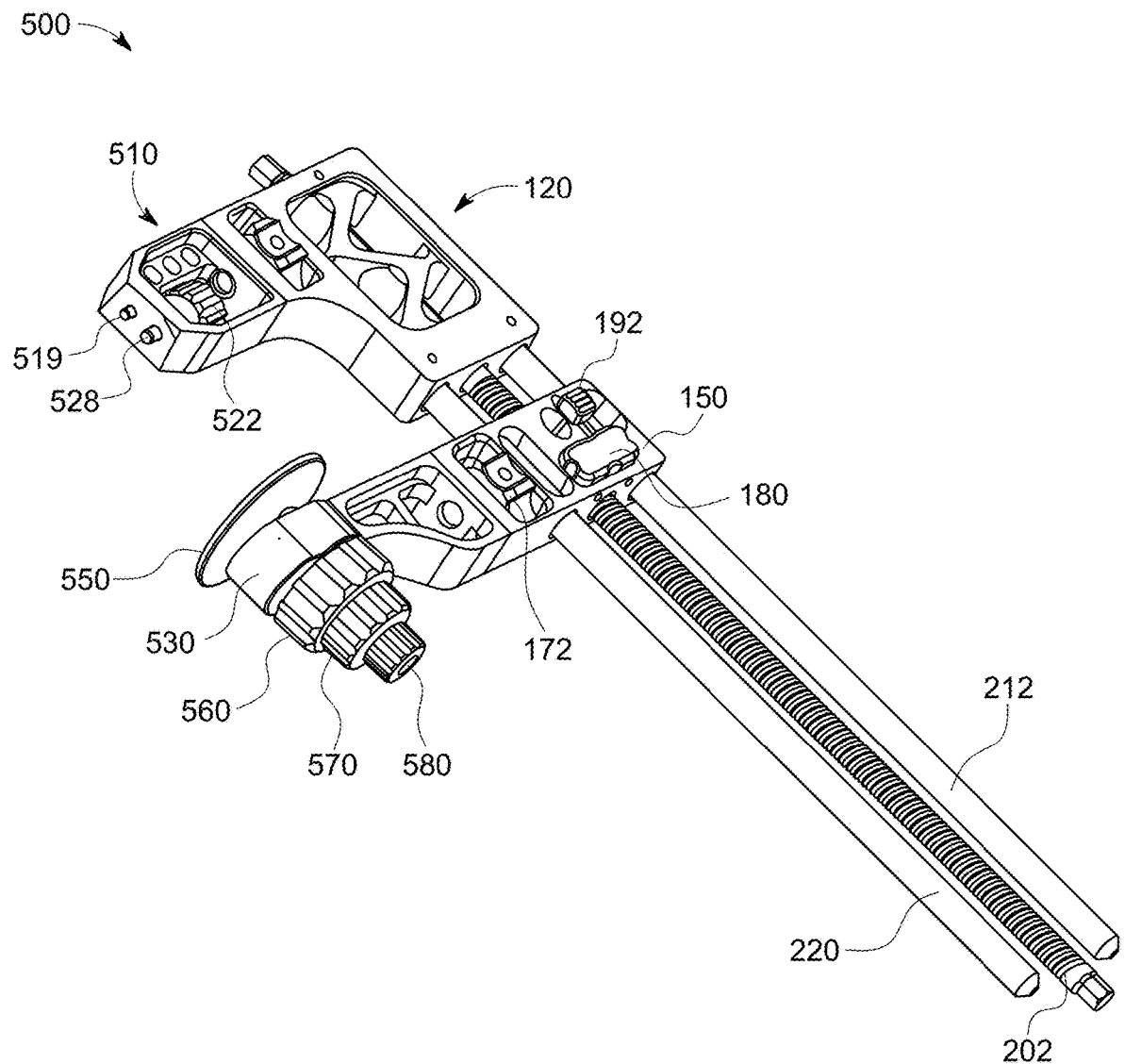
FIG. 28 is a first perspective view of another joint compression device, in accordance with an aspect of the present disclosure.
Figure 29:
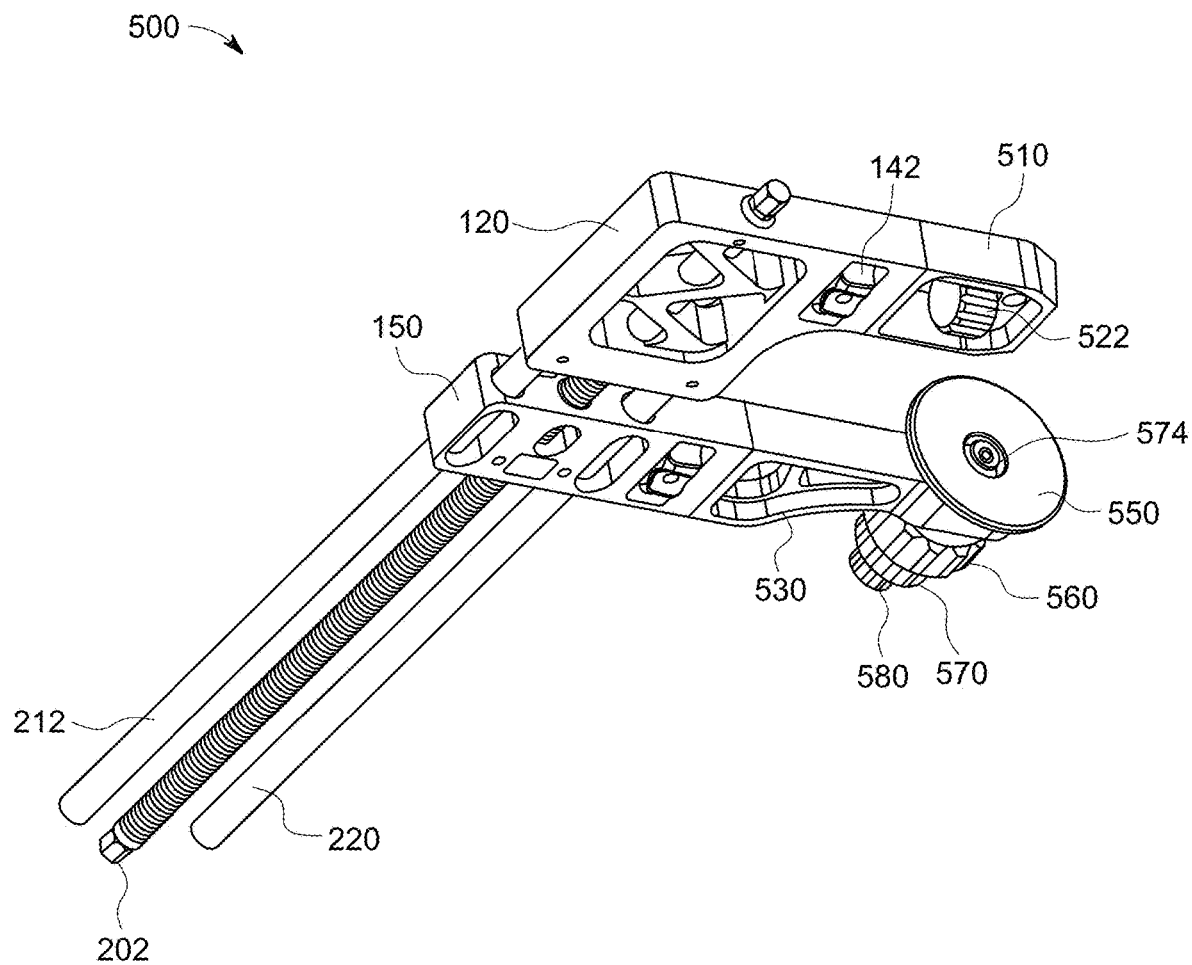
FIG. 29 is a second perspective view of the joint compression device of FIG. 28, in accordance with an aspect of the present disclosure.
Figure 30:
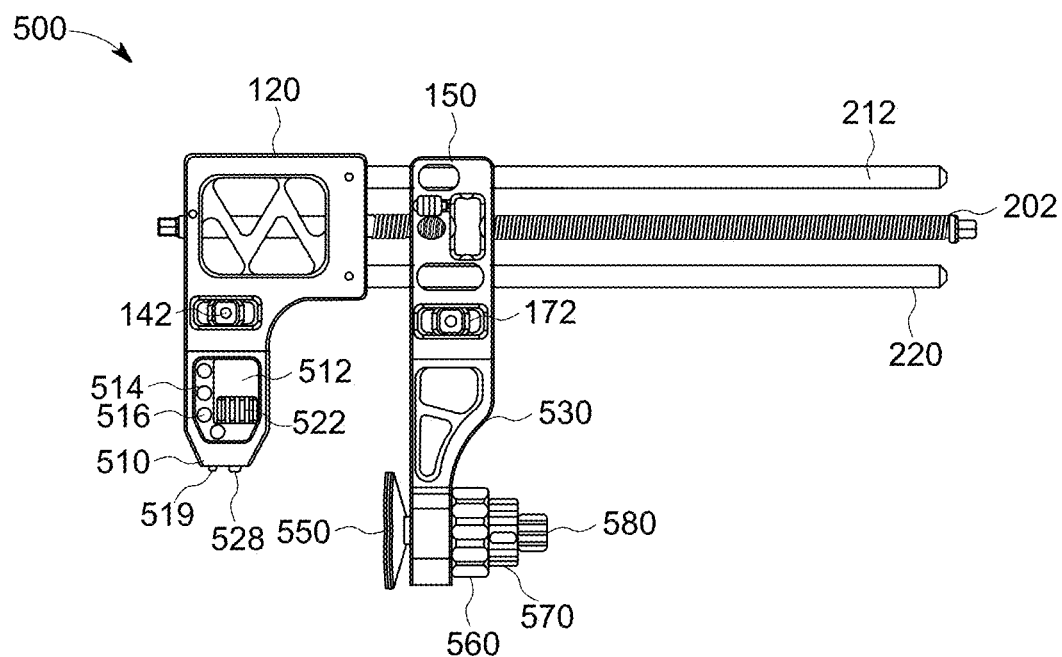
FIG. 30 is a top view of the joint compression device of FIG. 28, in accordance with an aspect of the present disclosure.
Figure 31:
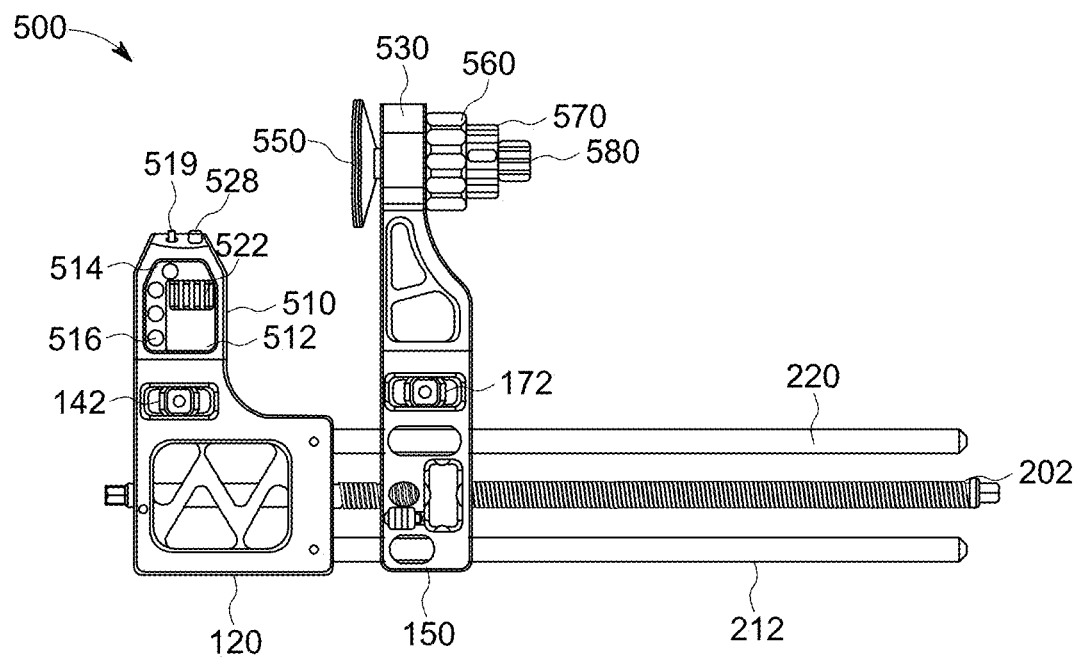
FIG. 31 is a bottom view of the joint compression device of FIG. 28, in accordance with an aspect of the present disclosure.
Figure 34:
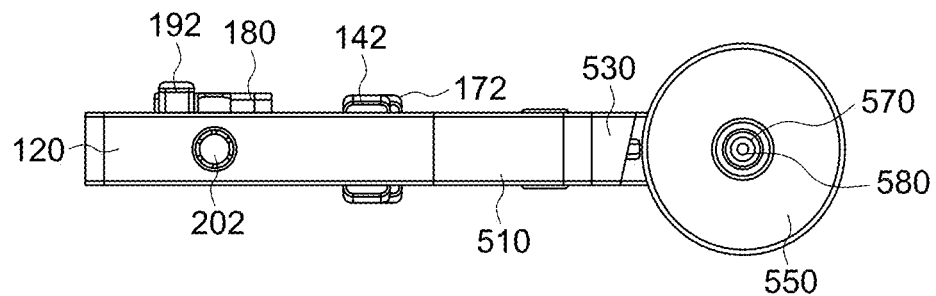
FIG. 34 is a first end view of the joint compression device of FIG. 28, in accordance with an aspect of the present disclosure.
Figure 35:
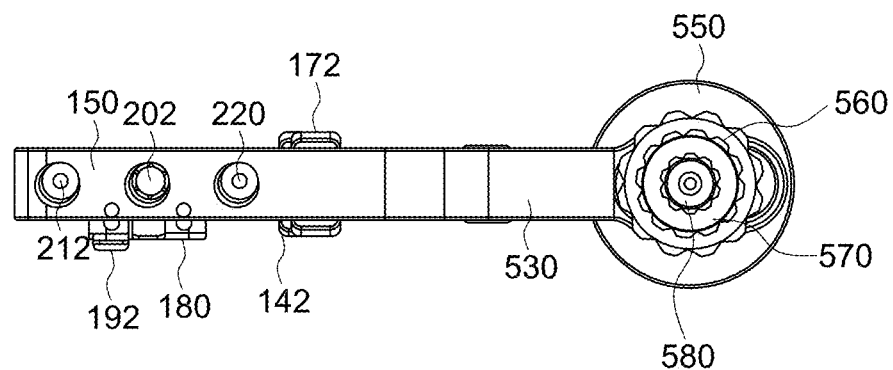
FIG. 35 is a second end view of the joint compression device of FIG. 28, in accordance with an aspect of the present disclosure.

With reference to FIGS. 25-27, a method of using the second joint compression device 400 may include inserting a guide wire 406 in a medial-lateral trajectory through the tibia a set distance from the bottom of the patient's foot. The distance may be, for example, 17 cm from the bottom of the foot. After the guide wire 406 is in place, the first members 120 with the attached arms 410 are inserted over the guide wire 406. The foot plate assembly 400 is then slid over the screws 202 and bars 212, 220 and the second members 150 are installed onto the screws 202 and bars 212, 220. The tibiotalar joint can then be compressed by turning the screws 202. In addition, the foot plate adjustment screw 460 may be rotated to adjust the first members 120 either anterior or posterior. After compression is achieved, the joint may be fixed.

Figure 36:
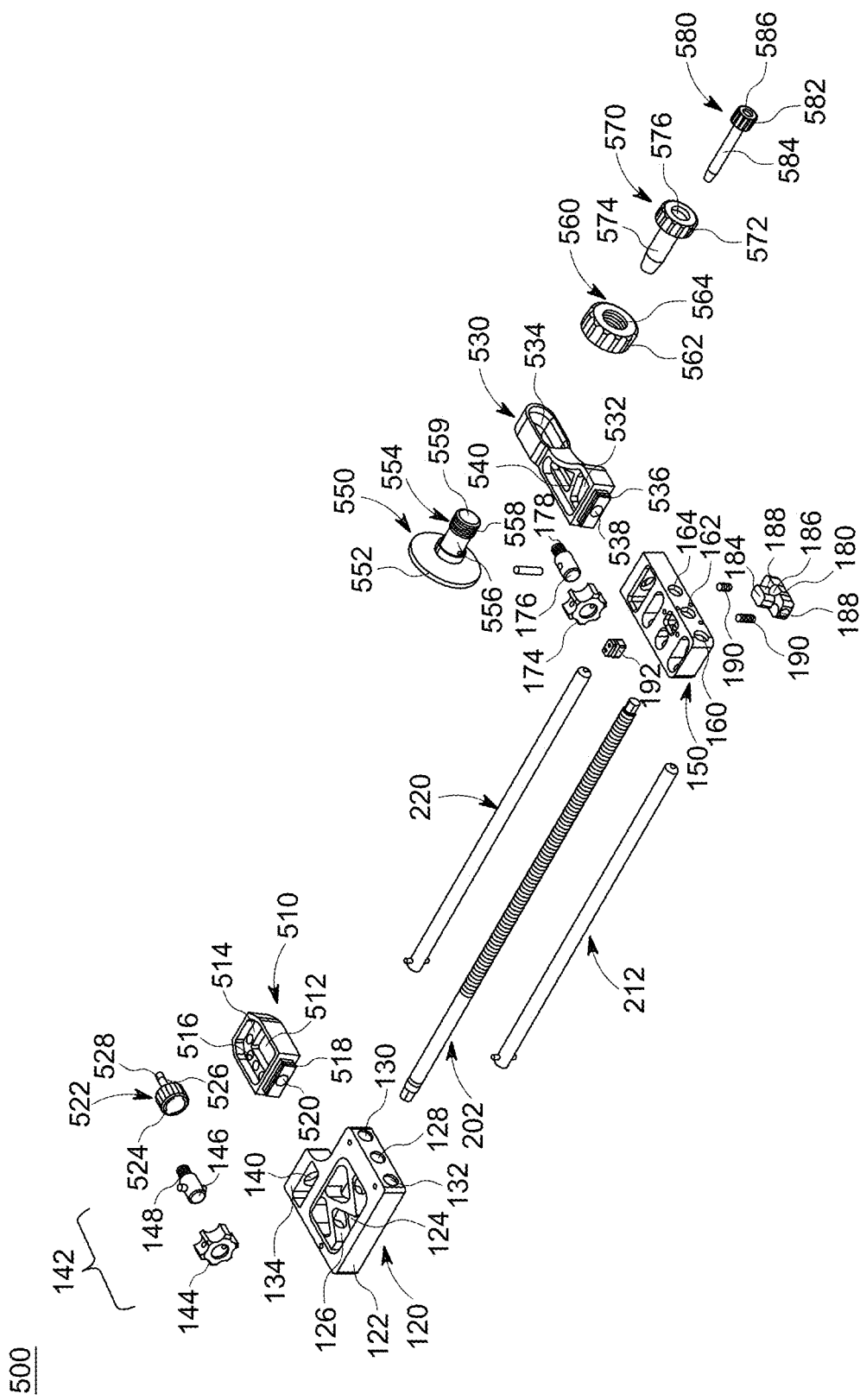
FIG. 36 is an exploded, first perspective view of the joint compression device of FIG. 28, in accordance with an aspect of the present disclosure.
Figure 37:
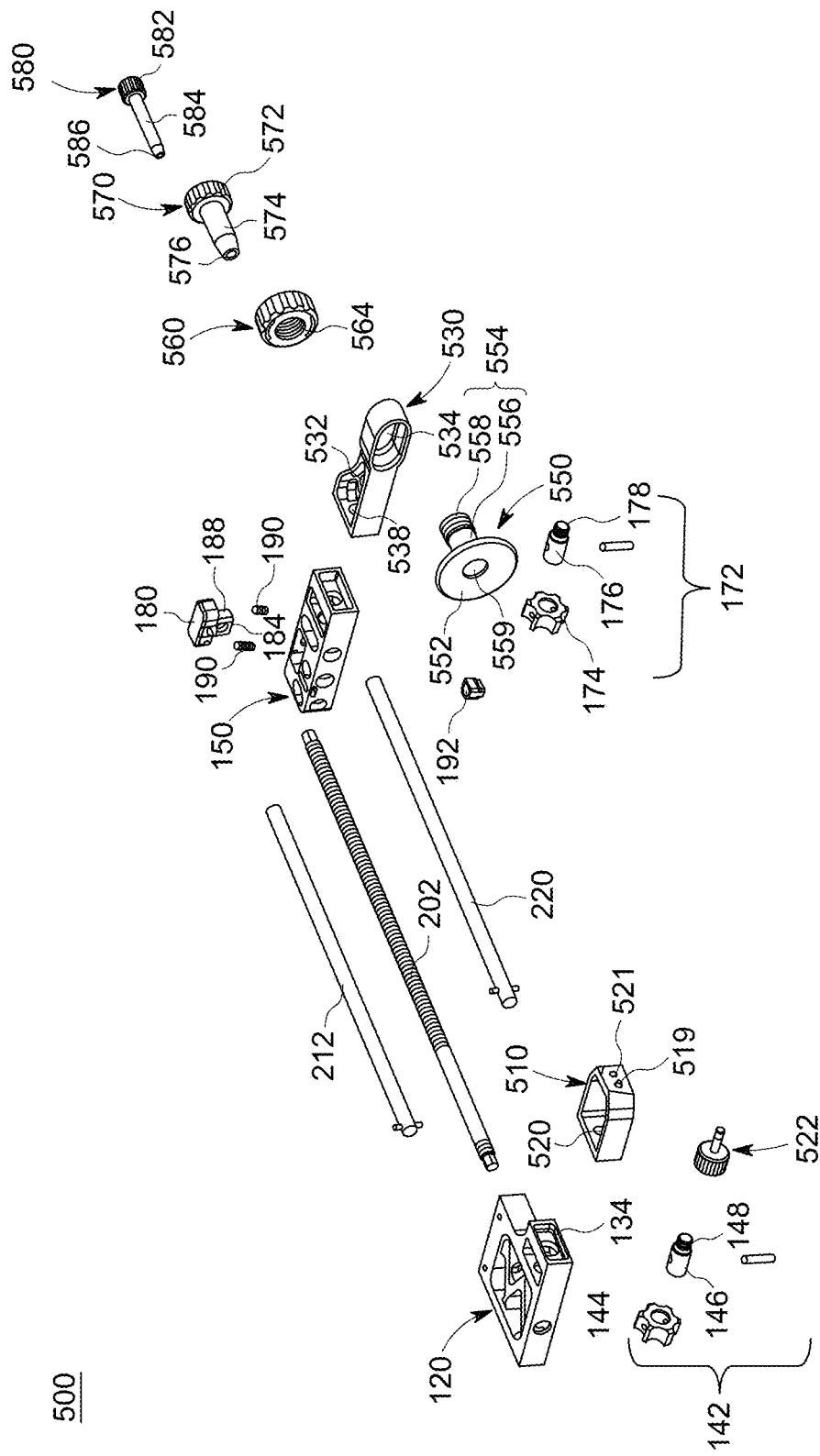
FIG. 37 is an exploded, second perspective view of the joint compression device of FIG. 28, in accordance with an aspect of the present disclosure.

Referring now to FIGS. 28-39, and more specifically FIGS. 36 and 37, a third joint compression device 500 is shown. The third joint compression device 500 includes a base system 110, a first arm 510, a second arm 530, a foot engagement member 550, a knob 560, drill guide tube 570, and a guide wire tube 580. The first arm 510 may include an opening 512 extending through the first arm 510 from a top surface to a bottom surface. The first arm 510 may also include a recessed region 514 surrounding the opening 512. The recessed region 514 may include a plurality of holes 516 extending through the recessed region 514. The first arm 510 may also include a protrusion 518 extending away from a first side of the first arm 510. The protrusion 518 may be, for example, sized and shaped or configured to be received within the recessed region 138 of the first member 120. The first arm 510 may also include a first through hole or threaded hole 520 for receiving the threaded portion 148 of the attachment member 142. In addition, the first arm 510 may include an alignment pin 519 extending away from a second side of the first arm 510 and a second through hole 521 extending from an exterior surface of the first arm 510 through to the opening 512, as shown in FIG. 37.

With continued reference to FIGS. 36 and 37, the first arm 510 may also include a set screw 522. The set screw 522 may include a knob 524 and a shaft 526 coupled to the knob 524. The shaft 526 may include a groove 528 extending around the circumference of the shaft 526. The groove 528 may rotatably secure the set screw 522 within the second through hole 521. Once the alignment pin 519 is inserted into a corresponding opening in the bone plate 600, the set screw 522 may be inserted into a corresponding opening to secure the third joint compression device 500 to the plate 600.

The second arm or subtalar targeting arm 530 may include an opening 532 extending through the second arm 530 from a top surface to a bottom surface, as shown in FIGS. 36 and 37. The second arm 530 may also include a through hole 534 extending through the first end to the second end. The through hole 534 may extend through the second arm 530 in a direction perpendicular to the opening 532. The second arm 530 may further include a protrusion 536 extending away from a side of the second arm 530. The protrusion 536 may also include a hole or threaded hole 538 extending through the second arm 530 from an exterior surface to the opening 532. The opening 532 may include at least one support structure 540 extending across the opening 532.

With continued reference to FIGS. 36 and 37, the heel pad or foot engagement member 550 includes a base portion 552 and a coupling portion 554. The coupling portion 554 extends away from a bottom surface of the base portion 552. The base portion 552 is configured or sized and shaped to engage the heel of a patient. The coupling portion 554 may include a shaft 556 with a threaded portion 558 extending along at least a portion of the shaft 556. The shaft 556 of the foot engagement member 550 may be received within the through hole 534 of the second arm 530. The foot engagement member 550 may also include a through hole 559 extending through the base portion 552 and the shaft 556.

The threaded knob 560 may include exterior protrusions 562 and a through hole or threaded hole 564, as shown in FIGS. 36 and 37. The threaded hole 564 may engage the threaded portion 558 of the foot engagement member 550 to couple the foot engagement member 550 to the second arm 530. The drill guide tube 570 may include a knob 572 with a shaft 574 extending away from an end of the knob 572. The drill guide tube 570 may also include a through hole 576 extending through the knob 572 and shaft 574 along the longitudinal axis. The shaft 574 of the drill guide tube 570 may be inserted into the through hole 559 of the foot engagement member 550. The guide wire tube 580 may also include a knob 582 with a shaft 584 extending away from an end of the knob 582. The guide wire tube 580 may also include a through hole 586 extending through the knob 582 and shaft 584 along the longitudinal axis. The shaft 584 of the guide wire tube 580 may be inserted into the through hole 576 of the drill guide tube 570.

Figure 38:
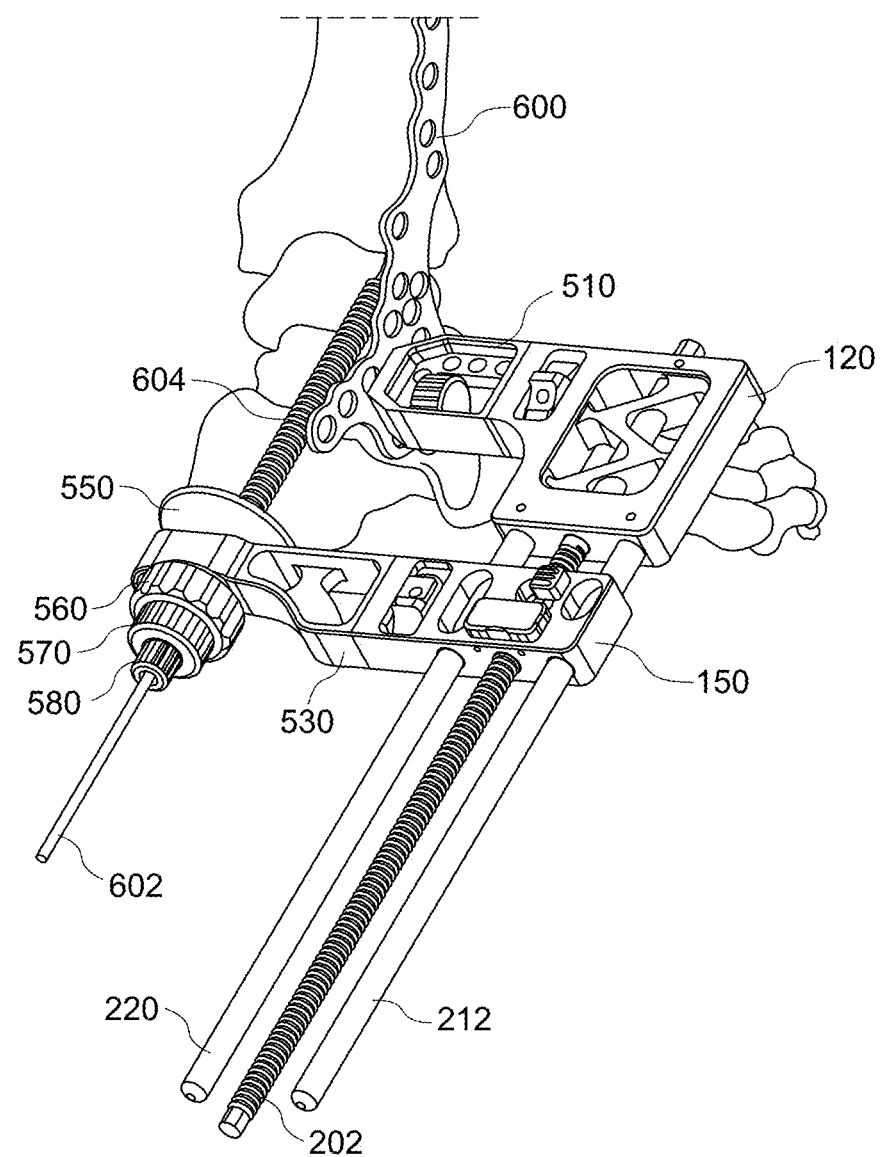
FIG. 38 is a first perspective view of the joint compression device of FIG. 28 positioned on a foot, in accordance with an aspect of the present disclosure.
Figure 39:
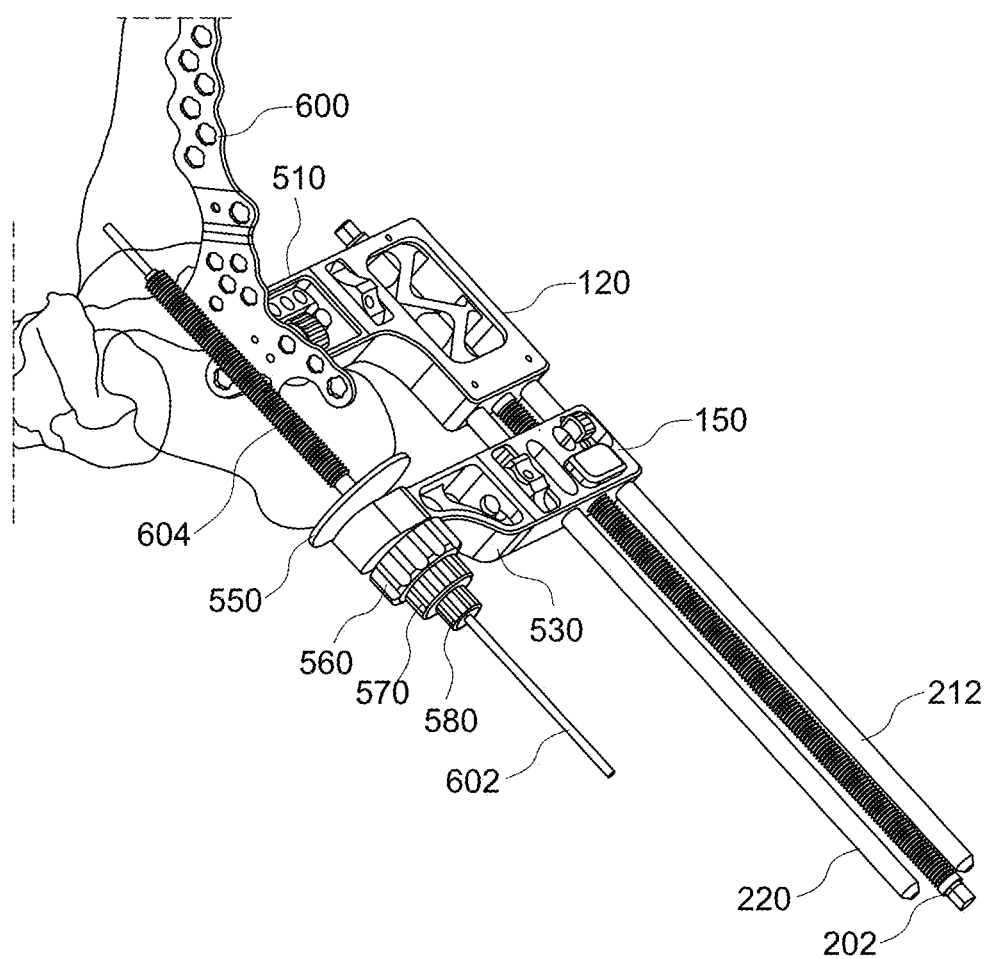
FIG. 39 is a second perspective view of the joint compression device of FIG. 38, in accordance with an aspect of the present disclosure.

Referring now to FIGS. 38 and 39, the third joint compression device 500 the base system 110 may be used with the arms 510, 530 to implant a lateral tibiotalocalcaneal (TTC) fusion plate 600. For implantation the first arm 510 is coupled to the first member 120 and the second arm 530 is coupled to the second member 150 using the attachment members 142, 172. The plate 600 may be coupled to the joint compression device 500 using the set screw 522. Then the coupled second member 150, second arm 530, foot engagement member 550, threaded knob 560, drill guide tube 570, and guide wire tube 580 may be coupled to the screw 202 and bars 212, 220 and positioned on a patient's heel. A guide wire or k-wire 602 may then be inserted through the foot engagement member 550, drill guide tube 570 and guide wire tube 580 and across the patient's anatomy. After the guide wire 602 is in place in the patient's foot, the screw 202 may be rotated and the subtalar joint compressed. Once the joint is compressed, the guide wire tube 580 may be removed and a drill (not shown) is inserted through the drill guide tube 570 to drill an opening for a bone screw 604. Next, the drill guide tube 570 is removed and a bone screw 604 may be inserted through the through hole 559 in the foot engagement member 550. As the opening 534 is an elongate opening 534, the knob 560 may be loosened and the foot engagement member 550 may be translated within the opening 534 in a medial or lateral direction to allow the surgeon to adjust the trajectory of the screw 604.

Referring now to FIGS. 40-43, a fourth plate fusion system or compression device 700 is shown. The joint compression device 700 includes the base system or parallel bar compression system 710. The base system 710 includes a first member or parallel bar rack 720, a second member or threaded engagement block 750, a translating member or lead screw 202, a first bar 212, and a second bar 220, as shown in at least FIGS. 40-43. The first member 720 is coupled to the second member 750 by the translating member 202, the first bar 212, and the second bar 220. The translating member 202, first bar 212, and second bar 220 extend between the first member 720 and the second member 750 positioned parallel to each other. The translating member 202, first bar 212 and second bar 220 are the same or similar to as described in greater detail above with reference to joint compression devices 100, 400, 500 and will not be described again here in detail for brevity sake.

Figure 42:
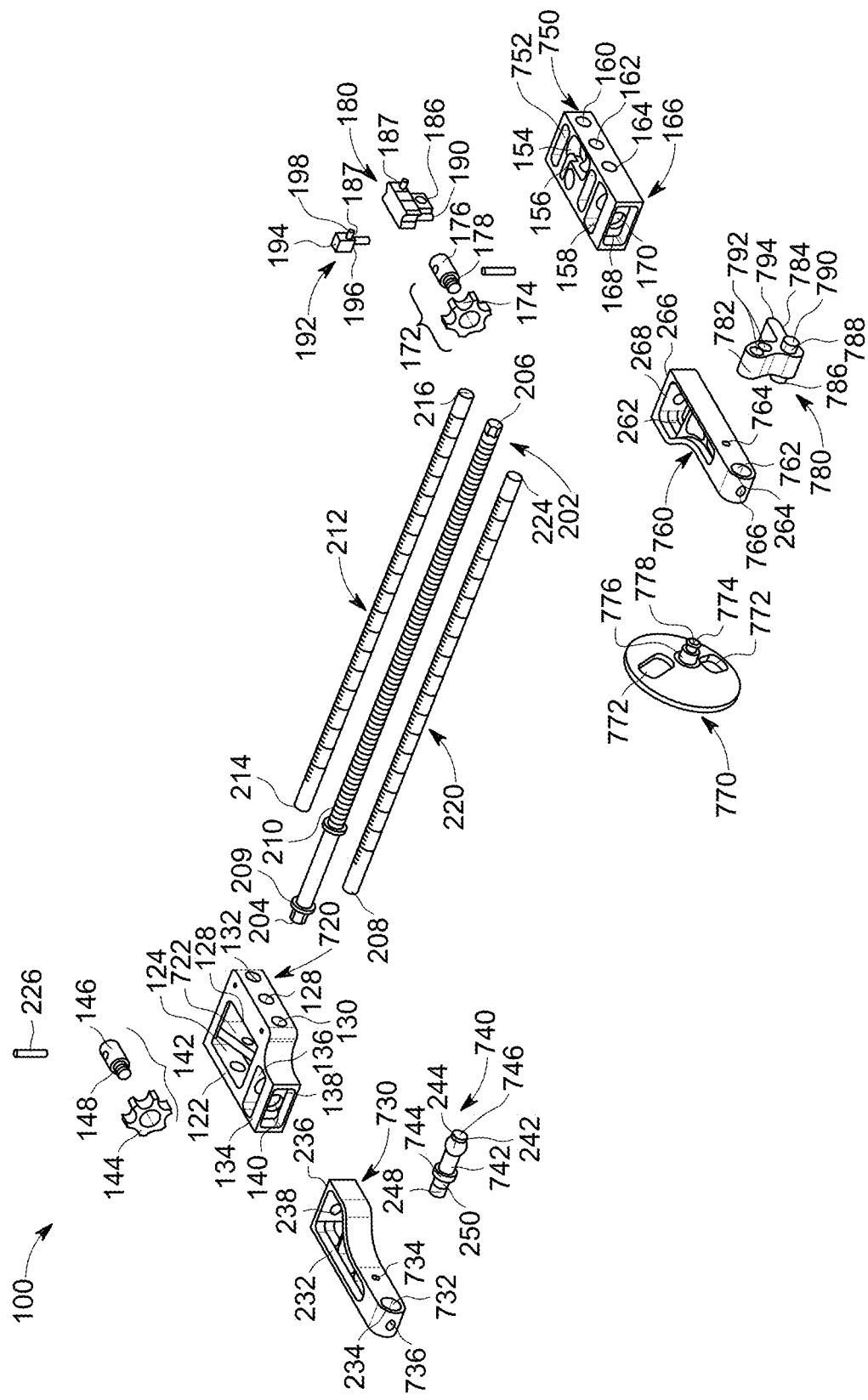
FIG. 42 is an exploded, first perspective view of the joint compression device of FIG. 40, in accordance with an aspect of the present disclosure.
Figure 43:
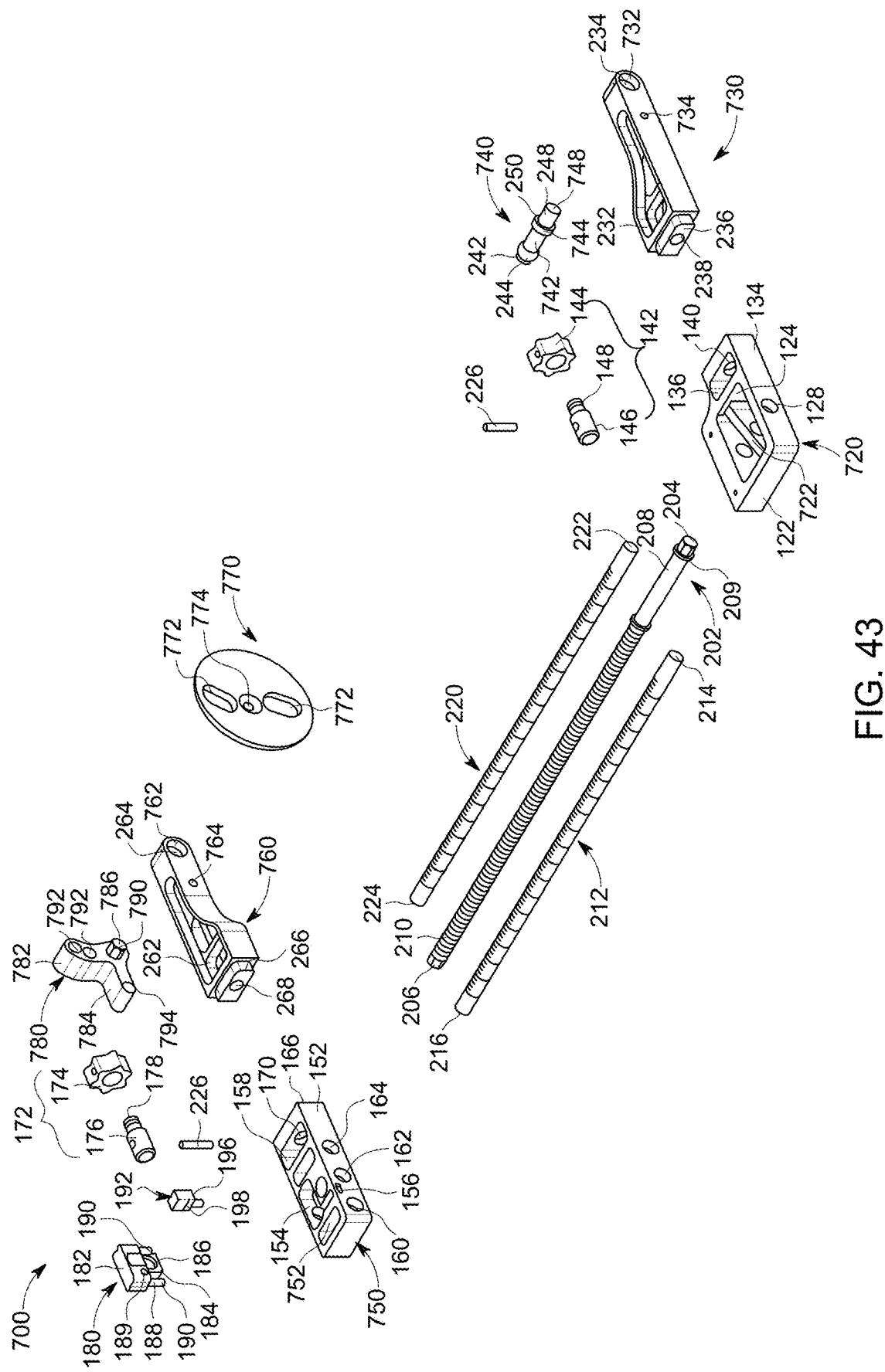
FIG. 43 is an exploded, second perspective view of the joint compression device of FIG. 40, in accordance with an aspect of the present disclosure.
Figure 44:
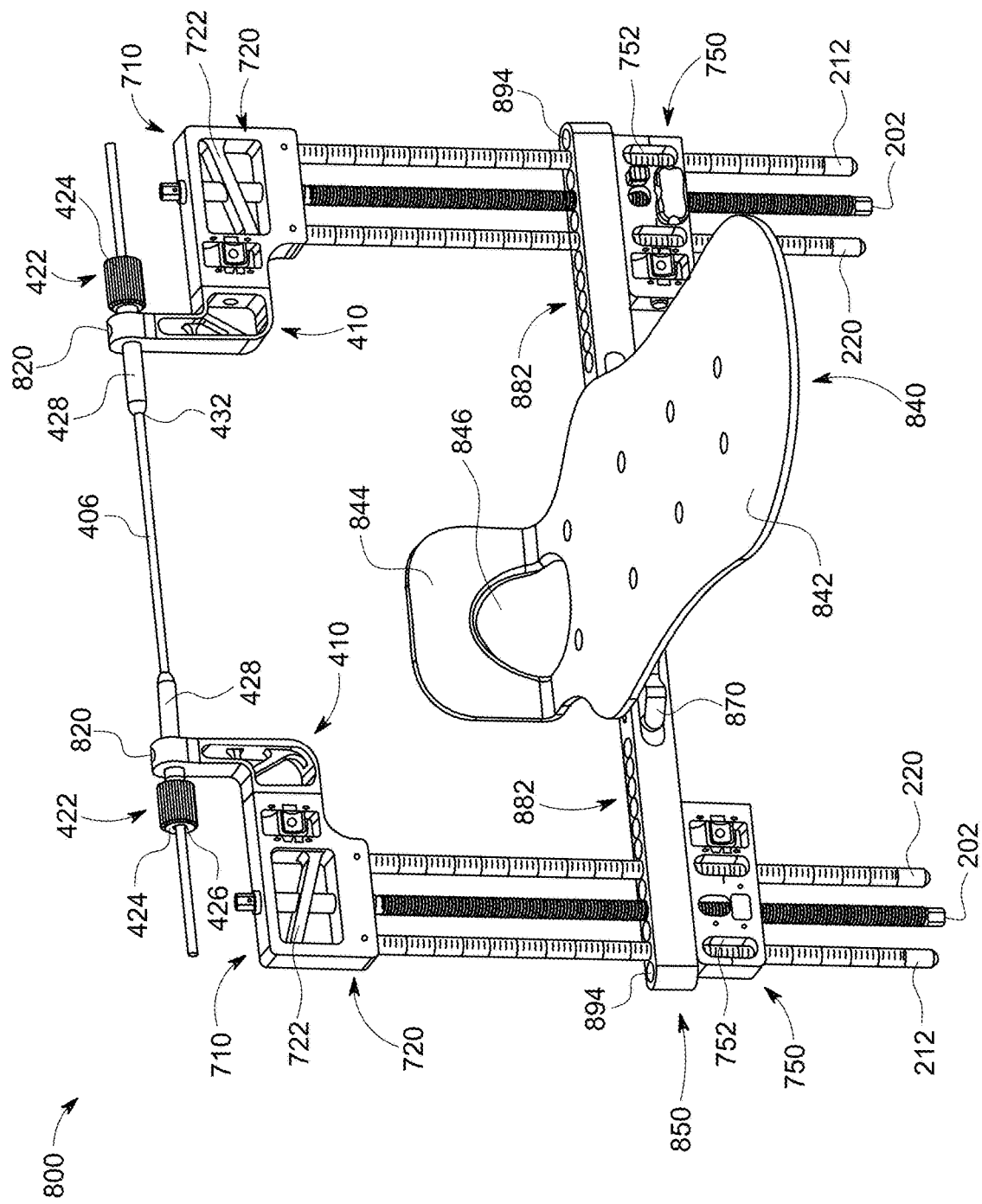
FIG. 44 is a first perspective view of a further joint compression device, in accordance with an aspect of the present disclosure.
Figure 45:
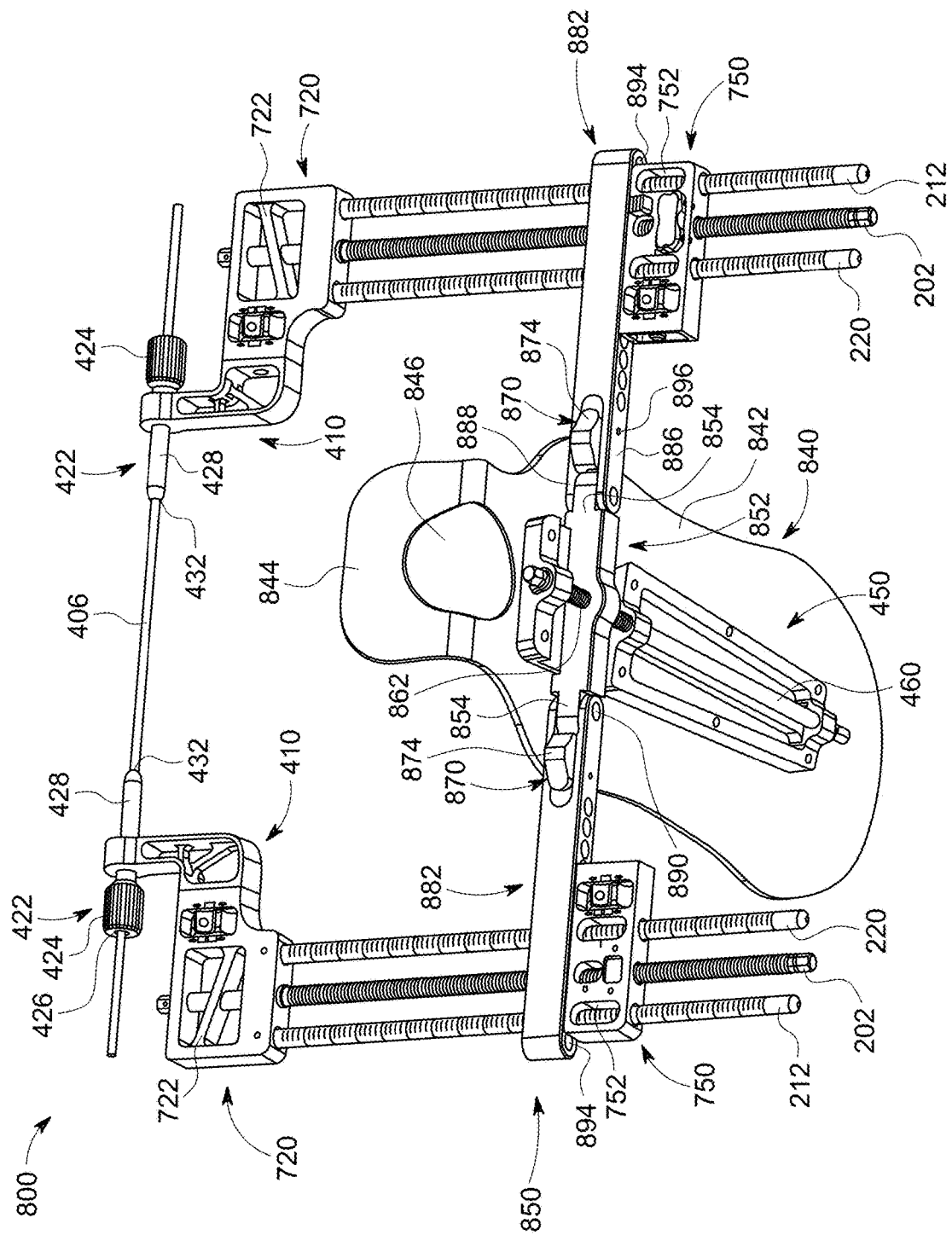
FIG. 45 is a second perspective view of the joint compression device of FIG. 44, in accordance with an aspect of the present disclosure.

The first member 720 includes a body 122 with a foot member 134 extending away from the body 122 on one side of the first member 720. The exterior configuration of the body 122 and the foot member 134 may be the same or similar to as described in greater detail above and which will not be described again here for brevity sake. The first member 720 also includes the opening 124 as described in greater detail above. However, the opening 124 in first member 720 may include, for example, an alternative support member 722. The at least one support member 722 may extend across the opening 124. As shown, the at least one support member 722 includes one support member extending, for example, diagonally across the opening 124. Alternative numbers of support members 722 and positions of the support member 722 are also contemplated. The first member 720 also includes a through hole 128, the same or similar to the through hole 128 described in greater detail above with reference to compression devices 100, 400, 500. The through hole 128 may, for example, extend through at least a portion of the at least one support member 722 as the through hole 128 extends across the opening 124. The first member 720 also includes a first hole 130, a second hole 132, and a third hole 140, as shown in FIG. 43. The first hole 130, the second hole 132, and the third hole 140 may be as described in greater detail above with respect to compression devices 100, 400, 500 and will not be described again here, in detail, for brevity sake. As shown in FIGS. 42 and 43, the first member 720 may also include an attachment member 142 received within the foot member 134, as described in greater detail above with respect to compression devices 100, 400, 500 and will not be described again here, in detail, for brevity sake.

The second member 750 may include a body 152 with a first opening 154 extending through the body 152 from a top surface to a bottom surface and a channel 156 extending away from a portion of the first opening 154 and into the body 152, as shown in FIGS. 42 and 43. The body 152 may also include a second opening 158 extending through the body 152 from the top surface to the bottom surface. The body 152 may further include a first through hole 160, a second through hole 162, and a third through hole 164. The first opening 154, channel 156, second opening 158, first through hole 160, second through hole 162, third through hole 164 may be as described in greater detail above with respect to compression devices 100, 400, 500 and will not be described again here, in detail, for brevity sake.

Figure 40:
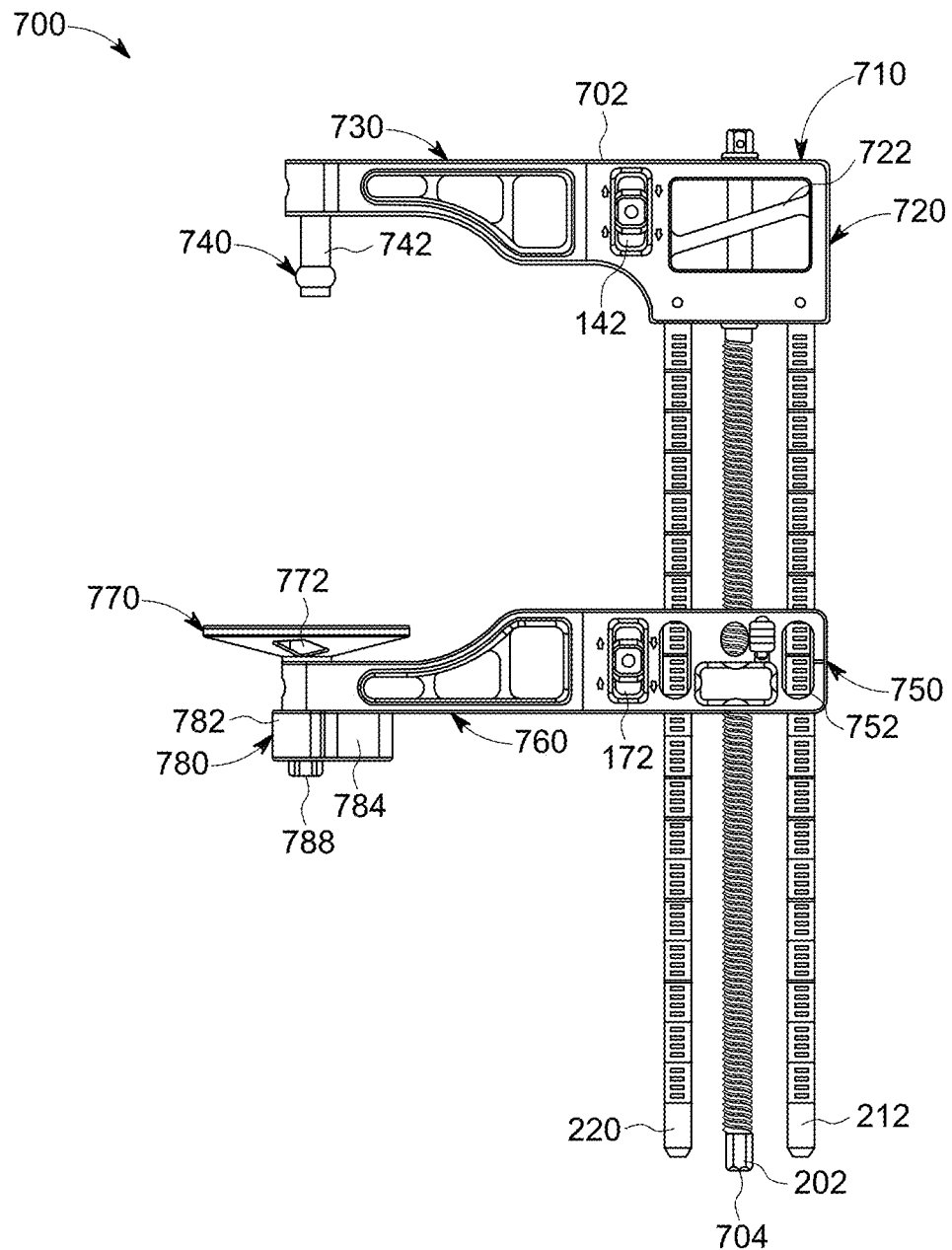
FIG. 40 is a top view of another joint compression device, in accordance with an aspect of the present disclosure.
Figure 41:
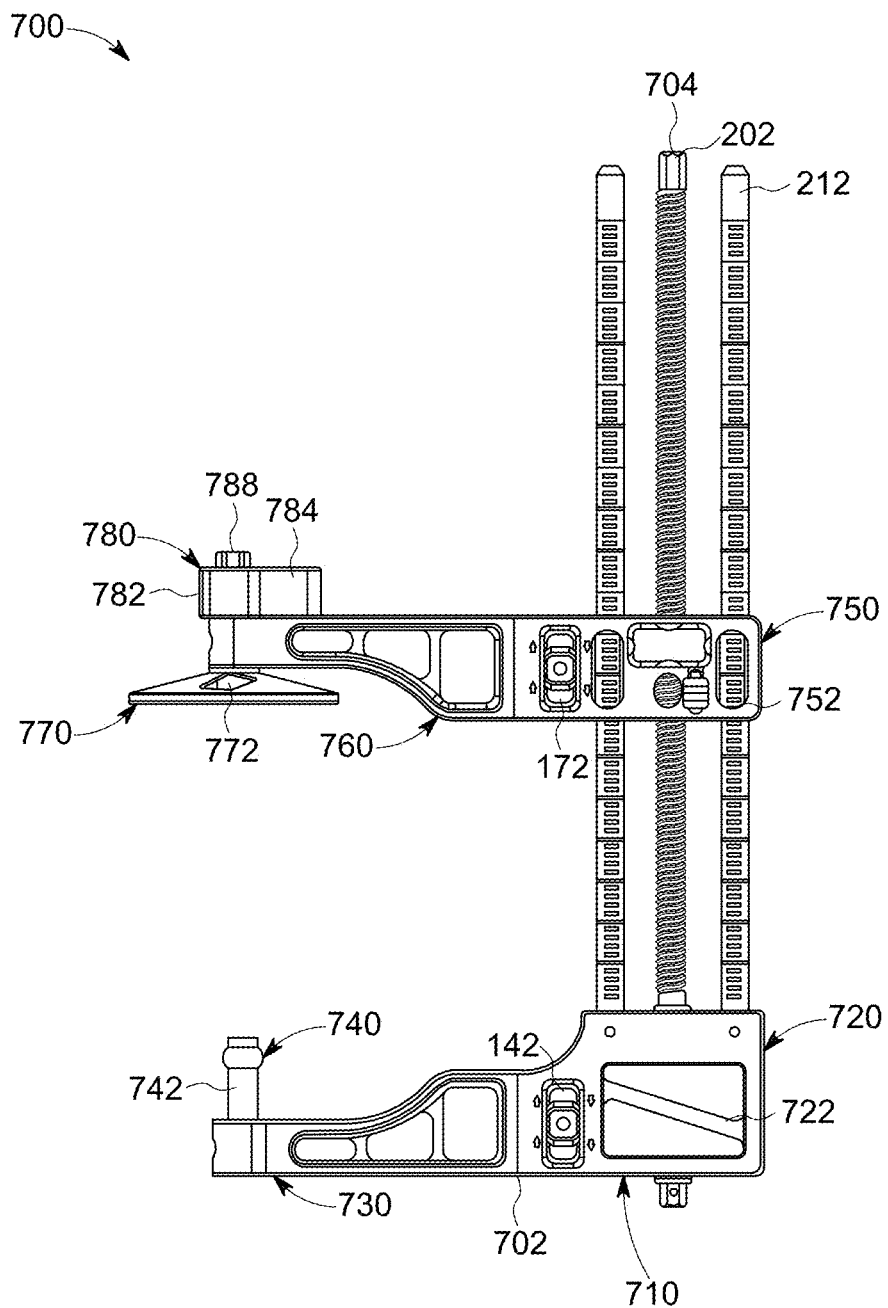
FIG. 41 is a bottom view of the joint compression device of FIG. 40, in accordance with an aspect of the present disclosure.

With reference to FIG. 42, the second member 750 may also include the engagement end 166 with a recessed region 168 and a hole 170, as described in greater detail above and which will not be described again here for brevity sake. As shown in FIGS. 42 and 43, the second member 750 may also include an attachment member 172 received within the second member 750. The attachment member 172 may include a knob 174 and a shaft 176 that extends through an opening in the knob 174. The attachment member 172 may be as described in greater detail above with reference to compression devices 100, 400, 500 and which will not be described again here for brevity sake. The second member 750 may also include a button 180 received within the first opening 154 and a lock or engagement lock switch 192 received within the channel 156, as shown in FIGS. 40 and 41. The button 180 and lock 192 may be as described in greater detail above with reference to compression devices 100, 400, 500 and which will not be described again here for brevity sake.

The fourth compression device 700 also includes a first arm 730, and a second arm 760. The system 100 may also include a tube or plate engagement tube 740 and a k-wire guide 780. Further, the system 700 may include the plate 300, guide wires or k-wires 256, 258, a first fastener 310, and a second fastener 320, as shown in FIGS. 11 and 12. The first arm 730 may be, for example, similar to the first arm 230 as described in greater detail above with the differences described in greater detail below. The first arm 730 includes an opening or window 232 extending through the first arm 730 from a top surface to a bottom surface. The first arm 730 also includes a through hole 234 extending through a second end of the first arm 730 from a first end to a second end. The through hole 234 may extend through the first arm 730 perpendicular to the opening 232. The first arm 730 may also include a protrusion 236 extending away from a first end of the first arm 730. The protrusion 236 may be, for example, sized and shaped to be received within the recessed region 138 of the first member 720. The first arm 730 may further include a coupling opening or threaded opening 238 extending from an exterior surface through the protrusion 236. The coupling opening 238 may be, for example, sized and shaped to receive the threaded portion 148 of the attachment member 142.

The plate engagement tube or tube 740 may be, for example, similar to tube 240 with the stop member 246 replaced by an intermediate shaft portion 742 and a stop member or protrusion 744. The tube 740 may include an engagement end 242 for contacting a bone plate, for example, bone plate 300, as shown in FIGS. 11 and 12. The tube 740 may also include a hole engagement member 244 for engaging a corresponding hole 306 in the bone plate 300. The tube 740 may further include a stop member or protrusion 744 extending away from the second end of the intermediate shaft portion 742. A first end of the intermediate shaft portion 742 is coupled to and extends away from the engagement member 244. The protrusion 744 prevents the tube 740 from passing entirely through the through hole 234. The tube 740 may also include a shaft portion 248 extending away from the protrusion 744 on a side opposite the intermediate shaft portion 742. The shaft portion 248 may include a groove 250 positioned adjacent to the protrusion 744. The shaft portion 248 is inserted into the through hole 234 until the protrusion 744 engages the recessed region 732 in the first arm 730. The tube 740 may be secured to the first arm 730 by a pin (not shown) inserted into the opening 736 in the first arm 730 and engaging the groove 250 in the tube 740. In addition, the tube 740 may include a first hole 746 extending into a first end through the engagement member 244 and intermediate shaft portion 742 to the protrusion 744 along the longitudinal axis of the tube 740. The tube 740 may also include a second hole 748 extending into a second end through the shaft portion 248 to the protrusion 744 along the longitudinal axis of the tube 740.

With continued reference to FIGS. 42 and 32, the second arm 760 includes an opening or window 262 extending through the second arm 760 from a top surface to a bottom surface. The second arm 760 also includes a through hole 264 extending through a second end of the second arm 760 from a first end to a second end. The through hole 264 may extend through the second arm 760 perpendicular to the opening 262. The second arm 760 may also include a protrusion 266 extending away from a first end of the second arm 760. The protrusion 266 may be, for example, sized and shaped to be received within the recessed region 168 of the second member 750. The second arm 760 may further include a coupling opening or threaded opening 268 extending from an exterior surface through the protrusion 266. The coupling opening 268 may be, for example, sized and shaped to receive the threaded portion 178 of the attachment member 172. The foot engagement member or heel pad 770 may be, for example, received within the through hole 264 of the second arm 760. The foot engagement member 770 may be, for example, sized and shaped or configured to receive a portion of a patient's heel. The foot engagement member 770 may be, for example, circular shaped and curved to form a concave surface for contacting or receiving a patient's heel. The engagement member 770 may include at least one widow or opening 772 extending through the engagement member 770 from a first side to a second side. The engagement member 770 may also include a shaft extending away from a bottom surface of the engagement member 770. The shaft includes a protrusion 776 coupled to the bottom surface of the engagement member 770. The shaft also includes a groove 778 extending circumferentially around the shaft and positioned adjacent to the protrusion 776. The groove 778 may be, for example, sized and shaped or configured for receiving a coupling member, such as a pin to secure the engagement member 770 to the second arm 760. The engagement member 770 and the shaft may each include a through hole 774 extending through the engagement member 770 and shaft. The through hole 774 may extend along the longitudinal axis of the engagement member 770.

With continued reference to FIGS. 42 and 43, the optional k-wire guide 780 may be positioned to align with the through hole 264 of the second arm 760. The k-wire guide 780 may include a first body portion or first leg 782 and a second body portion or second leg 784. A second end of the first body portion 782 is coupled to the first end of the second body portion 784. The guide 780 may have, for example, an "L" shape or "7" shape. The first body portion 782 and the second body portion 784 may be positioned to form an angle between, for example, 50° and 130°, more preferably between 80° and 100°, and approximately 90°. The first body portion 782 may, for example, curve with respect to a longitudinal axis extending perpendicular to the through hole 264. The second body portion 784 may extend, for example, perpendicular to the through hole 264 and linearly from the first body portion 782. The guide 780 may also include a first engagement protrusion 786 extending away from a first side of the guide 780 where the first and second body portions 782, 784 are coupled together. In addition, the guide 780 may include a second engagement protrusion 788 extending away from a second side of the guide 780. The protrusions 786, 788 may be, for example, sized and shaped or configured to be received within the recessed region 762 of the second arm 760. The guide 780 may also include a first through hole 790 extending through the protrusions 786, 788 and the coupled body portions 782, 784. The first through hole 790 may be, for example, sized and shaped or configured to receive a guide wire, k-wire, or the like fixator. The guide 780 may also include at least one second through hole 792 extending through the first body portion 782 from a first side to a second side and a third through hole 794 extending through the second body portion 784 from a first side to a second side. The through holes 790, 792, 794 may each extend through the guide 780 parallel to each other. The at least one second through hole 792 may be, for example, separate holes, overlapping holes, or a combination of separate and overlapping holes. The guide 780 may be used, for example, for insertion of at least one guide wire, k-wire or the like fixator through the first and second body portions 782, 784 and into the patient's foot.

Once assembled, as shown in FIGS. 40 and 41, the joint compression device 700 allows for the second member 750 to slide over the screw 202 and bars 212, 220 and to translate along the path of the screw 202 and bars 212, 220. The button 180 of the second member 750 may be depressed to disengage the threads 210 of the screw 202 and allow for rapid translation along the parallel screw 202 and bars 212, 220. When the button 180 is released, the button 180 engages the threads 210 of the screw 202. The engaged button 180 may be locked into place by engaging the engagement member 200 of the engagement lock 192, as shown in FIG. 42, with the locking opening 189 of the button 180, as shown in FIG. 43. The second member 750 translates along the screw 202 and bars 212, 220 independent of the first member 720. With continued reference to FIGS. 40 and 41, the screw 202 of the first member 720 may be rotated to allow the second member 750 to translate back and forth with respect to the first member 720. The attachment members 142, 172 of the first and second members 720, 750 allow for attachment of interchangeable arms for various procedures, as discussed in greater detail above.

With reference to the fourth joint compression device 700, the base system 710 may be used with the arms 730, 760 to implant, for example, an anterior tibiotalocalcaneal (TTC) fusion plate. For implantation, the arms 730, 760 are coupled to the first member 720 and second member 750, respectively, using the attachment members 142, 172. The tube 740 is then mated with the plate 300 and the foot engagement member 770 is placed on the desired target on the back of a patient's heel. A guide wire 256 is then inserted through the tube 740 and across the patient's bones and through the foot engagement member 770. Once the guide wire 256 is in place, the screw 202 may be rotated to compress the subtalar joint.

Referring now to FIGS. 44-47, a fifth plate fusion system or compression device 800 is shown. The joint compression device 800 includes a first base system 710, a first arm 410, a second base system 710, a second arm 410, and a foot plate assembly 840. The base systems 710 and arms 410 may be as described in greater detail above with respect to devices 400, 700 and which will not be described again here for brevity sake. The compression device 800 may also include a first k-wire guide tube 422, a second k-wire guide tube 422, and a guide wire or k-wire 406. The protrusions 416 of the arms 410 may be, for example, sized and shaped to be received within the recessed regions 138 of the first members 720.

Figure 46:
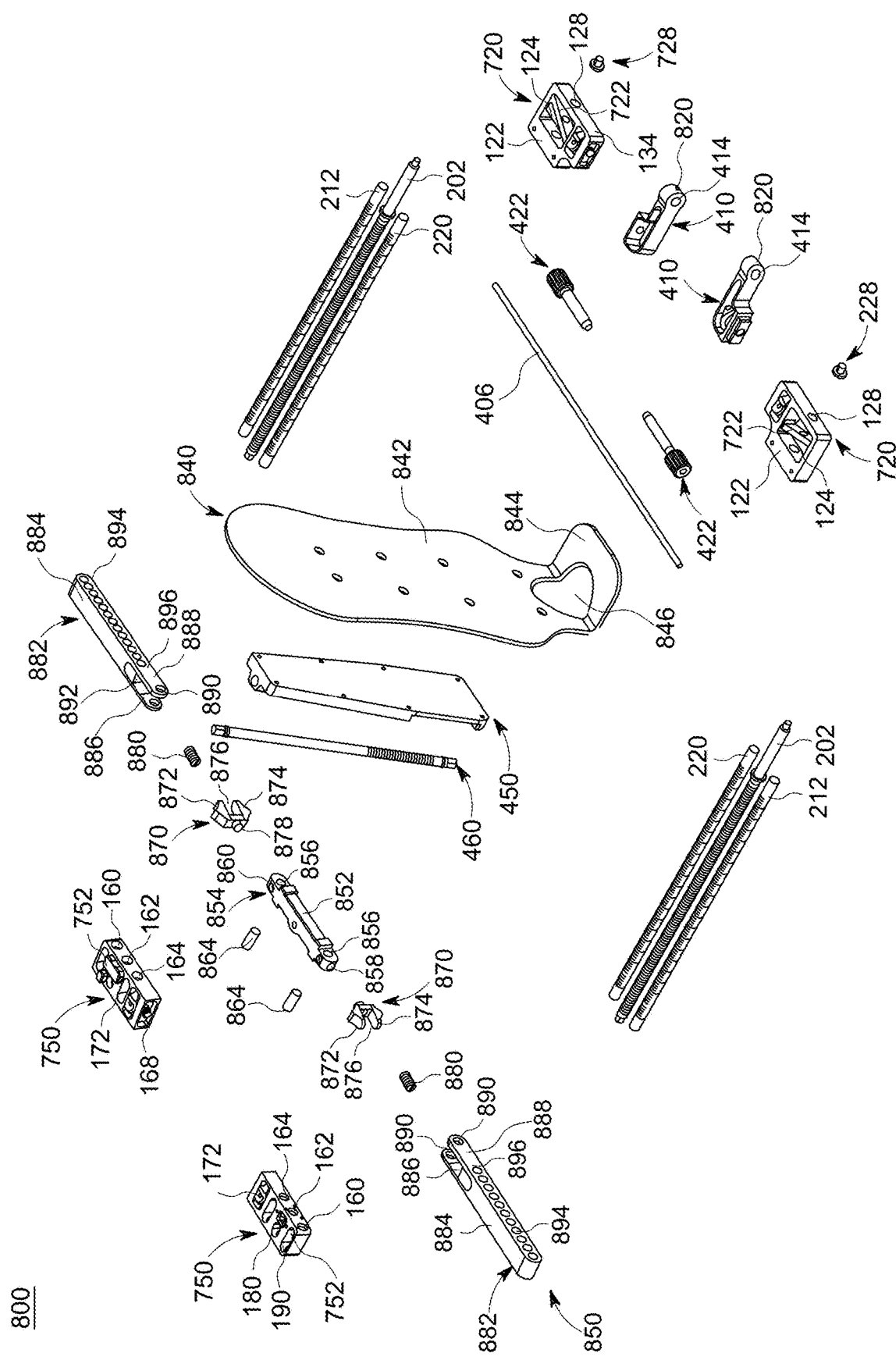
FIG. 46 is an exploded, first perspective view of the joint compression device of FIG. 44, in accordance with an aspect of the present disclosure.
Figure 47:
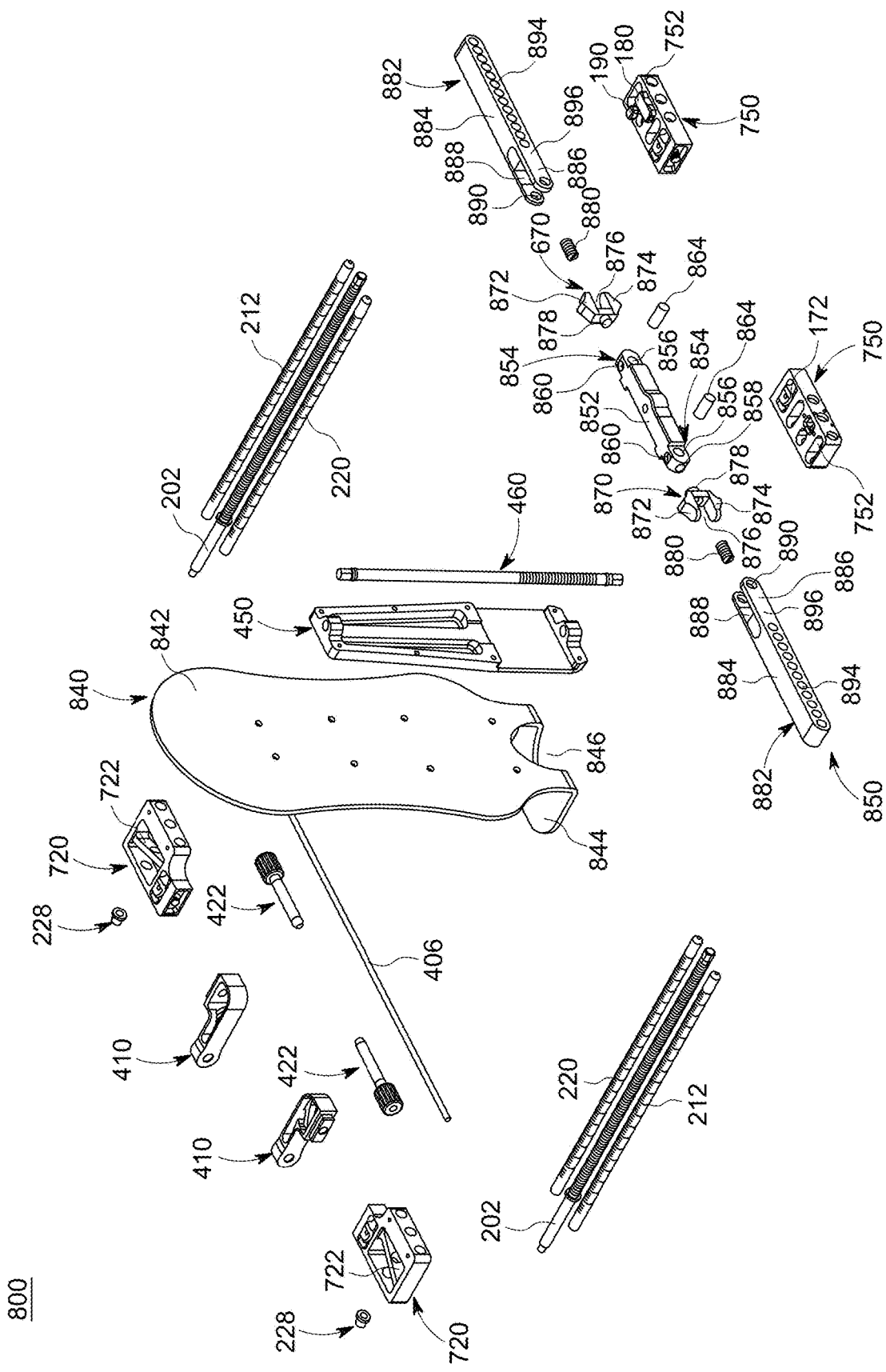
FIG. 47 is an exploded, second perspective view of the joint compression device of FIG. 44, in accordance with an aspect of the present disclosure.

With continued reference to FIGS. 44-47, the foot plate assembly 840 includes a foot plate 842, a foot plate adjustment base 450, a foot plate adjustment screw 460, and a foot plate adjustment bar 850. The foot plate 842 includes an extension 844 positioned perpendicular to the foot plate 842. The foot plate 842 may have, for example, a generally oval shape with curvatures positioned intermediate a first and second end. The foot plate adjustment base 450 is secured to a bottom surface of the foot plate 842. As shown in FIG. 47, the foot plate adjustment base 450 and the adjustment screw 460 may be as described in greater detail above with reference to device 400, which will not be described again here for brevity sake. The threaded portion 470 may engage a first through hole 862 on the foot plate adjustment bar 850.

The foot plate adjustment bar 850 also includes a base 852, a first securement member 870, a second securement member 870, a first arm 882 and a second arm 882, as shown in FIGS. 46 and 47. The base 852 has a first end and a second end. The first securement member 870 is positioned between the first arm 882 and the base 852. The second securement member 870 is positioned between the second arm 882 and the base 852. The first and second securement members 870 are slidably coupled to the base 852 and the arms 882. The base 852 may include a first coupling portion 854 at a first end and a second coupling portion 854 at a second end. The first and second coupling portions 854 may include a through hole 856 extending from a first side to a second side of the base 852. The coupling portions 854 may also include a cavity 858 extending into the coupling portions 854 from each end of the base 852 along a longitudinal axis. The cavities 858 may extend into the coupling portions 854 perpendicular to the through hole 856. The coupling portions 854 may also include a recess 860 extending into the coupling portions 854 from a side of the base 852. The recess 860 may be positioned, for example, aligned with the through hole 856. The base 852 may also include a threaded hole 862 positioned near a middle of the base 852. The threaded hole 862 may extend, for example, at least partially through a protrusion extending out from a side of the base 852. The base 852 may also have two protrusions extending away from the base 852 on a side opposite the protrusion for receiving at least a portion of the threaded hole 862.

With continued reference to FIGS. 46 and 47, the securement members 870 may include a first arm or first projection 872 extending parallel to a second arm or second projection 874. The projections 872, 874 may be positioned spaced apart from each other to form a passageway 876. The securement members 870 may also include, for example, a protrusion 878 extending away from an end of the securement member 870. The protrusion 878 may be positioned on a side opposite the projections 872, 874. The protrusions 878 may be inserted into the openings 858 of the base 852. As shown in FIGS. 46 and 47, the foot plate adjustment bar 850 also includes two spring members 880. The spring members 880 may be inserted into the passageways 876 of the securement members 870.

The arms 882 may include an arm base or base 884 with a first leg 886 and a second leg 888 extending away from a second end of the arm base 884. Each leg 886, 888 includes a through hole 890 extending through the legs 886, 888 from a first side to a second side. Coupling pins 864 may be inserted through the through hole 890 of the arms 882 and the through hole 856 of the base 852 to secure the arms 882 to the base 852. The spring members 880 and securement members 870 may be positioned between the arms 882 and base 852 when secured together. The projections 872, 874 of the securement members 870 may translate within recesses in the arm bases 884 to allow for translation of the securement members 870 and rotation of the arm base 884 relative to the base 852. The arm base 884 may also include a cavity 892 inset into the base 884 in a position between the legs 886, 888. The cavity 892 may be, for example, sized and shaped or configured to receive a spring member 880. The arm base 884 may also include a plurality of holes 894 extending through the base 882 from a first side to a second side. The holes 894 may be, for example sized and shaped or configured to receive screws 202 and bars 212, 220. The holes 894 may extend through the arm base 884 in a direction perpendicular to the passageway formed by the arms 886, 888. The arm base 884 may also include at least one locking pin hole 896 extending through the arm base 884 from the first side to the second side. The at least one locking pin hole 896 extends through the cavity 892 to secure the spring member 880 in the cavity 892.

With reference to the joint compression device 800, two base systems 710 may be used with the arms 410 and the foot plate assembly 840 to implant a tibiotalar (TT) fusion plate. For implantation, the joint compression device 800 may be assembled by coupling a first screw 202, a right first bar 212, and a right second bar 220 to a right first member 720 and a second screw 202, a left first bar 212, and a left second bar 220 to a left first member 720. A right arm 410 may then be coupled to the right first member 720 and a left arm 410 may be coupled to the left first member 720 using attachment members 142. The right and left guide tubes 422 may then be inserted into the right and left arms 410, respectively, and a guide wire or k-wire 406 may be inserted through the through holes 432 of the tubes 422. The first screw 202, the right first bar 212, and the right second bar 220 may be inserted through the plurality of holes 894 in the compressor bar 850. The second screw 202, the left first bar 212, and the left second bar 220 may be inserted through the plurality of third through holes 894 in the compressor bar 850. Once the compressor bar 850 is coupled to the screws 202 and bars 212, 220, the second members 750 may be coupled to the screws 202 and bars 220 and the second members 150 may contact the compressor bar 850. In addition, the coupled foot plate 842 and adjustment base 750 may be secured to the compressor bar 850 using the adjustment screw 460.

A method of using the joint compression device 800 may include, inserting a guide wire 406 in a medial-lateral trajectory through the tibia a set distance from the bottom of the patient's foot. The distance may be, for example, approximately 15 cm to 19 cm, and more preferably approximately 17 cm from the bottom of the foot. After the guide wire 406 is in place, the first members 720 with the attached arms 410 are inserted over the guide wire 406. The foot plate assembly 800 is then slid over the screws 202 and bars 212, 220 and the second members 150 are installed onto the screws 202 and bars 212, 220. The tibiotalar joint can then be compressed by turning the screws 202. In addition, the foot plate adjustment screw 460 may be rotated to adjust the first members 720 either anteriorly or posteriorly. After compression is achieved, the joint may be fixed.

In an alternative embodiment, the third plate compression system 500 may include a base system 710, a second member 750, a first arm 510, a second arm 530, a foot engagement member 550, a knob 560, drill guide tube 570, and a guide wire tube 580. In yet another alternative embodiment, the third plate compression system 500 could include the heel pad 770 and k-wire guide 780 in place of the foot engagement member 550, knob 560, drill guide tube 570, and guide wire tube 580. The base system 710, second member 750, heel pad 770, and k-wire guide 780 may be as described in greater detail above with reference to compression systems 700, 800 and which will not be described again here for brevity sake.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-14, FIGS. 15-27, FIGS. 28-39, FIGS. 40-43, and FIGS. 44-47 may be used interchangeably and in alternative combinations as would be modified or altered by one of skill in the art. Further, the steps of the surgical methods associated with the systems of FIGS. 1-14, FIGS. 15-27, FIGS. 28-39, FIGS. 40-43, and FIGS. 44-47 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiment, the invention is now claimed to be:

1. A joint compression device, comprising:
a base system, wherein the base system comprises:
 a first member, wherein the first member comprises:
  a body;
  a through hole extending through the body;
  a foot member extending from a side of the body;
  a knob opening extending through the foot member from a first side to a second side; and
  a recessed region extending into the foot member from a first end of the first member, wherein the knob opening extends into the first member perpendicular to the through hole;
 a second member;
 at least one parallel member coupling the first member to the second member, wherein the second member translates along the at least one parallel member; and
at least one arm coupled to the base system.

2. The joint compression device of claim 1, wherein the first member further comprises:
an opening extending through at least a portion of the body from a first side to a second side; and
at least one supporting member extending across the opening; and
wherein the through hole extends through the at least one supporting member.

3. The joint compression device of claim 1, wherein the at least one parallel member comprises:
a screw.

4. The joint compression device of claim 1, wherein the at least one parallel member further comprises:
at least one bar.

5. The joint compression device of claim 1, wherein the at least one arm comprises:
a first arm coupled to the first member; and
a second arm coupled to the second member.

6. The joint compression device of claim 5, wherein the first arm comprises:
a window extending through the first arm from a first side to a second side;
a through hole extending through the first arm from a third side to a fourth side, wherein the window extends through the first arm perpendicular to the through hole; and
a protrusion extending away from a second end of the first arm, wherein the protrusion engages the recessed region of the first member.

7. The joint compression device of claim 6, wherein the second member comprises:
a body;
a first through hole extending through the body from a first side to a second side;
a second through hole extending through the body from the first side to the second side; and
a third through hole extending through the body from the first side to the second side;
wherein the first through hole, the second through hole and the third through hole movably receive the at least one parallel member.

8. The joint compression device of claim 7, wherein the second member further comprises:
an opening extending through the body from a third side to a fourth side;

an attachment member received within the opening, wherein the attachment member rotates within the opening;

an engagement end positioned at a second end of the body; and a recessed region extending into the engagement end of the body.

9. The joint compression device of claim 8, wherein the second arm comprises:
a window extending through the second arm from a first side to a second side;
a through hole extending through the second arm from a third side to a fourth side, wherein the window extends through the second arm perpendicular to the through hole; and
a protrusion extending away from a second end of the second arm, wherein the protrusion engages the recessed region of the second member.

10. The joint compression device of claim 9, further comprising:
a plate engagement tube removably coupled to the first arm, wherein the plate engagement tube is received within the through hole of the first arm; and
a foot engagement member removably coupled to the second arm, wherein the foot engagement member is received within the through hole of the second arm.

11. The joint compression device of claim 1, further comprising:
a second base system; and
wherein the at least one arm comprises:
a first arm coupled to the base system; and
a second arm coupled to the second base system; and
wherein the base system is coupled to the second base system by a guide wire inserted through the first arm on a first end and the second arm on a second end.

12. The joint compression device of claim 11, further comprising:
a foot plate assembly.

13. A joint compression device, comprising:
a base system, comprising:
a first base system, comprising:
a first member;
a second member; and
at least one parallel member coupling the first member to the second member, wherein the second member translates along the at least one parallel member;
a second base system; and
at least one arm coupled to the base system, wherein the at least one arm comprises:
a first arm coupled to the first base system; and
a second arm coupled to the second base system; and
wherein the first base system is coupled to the second base system by a guide wire inserted through the first arm on a first end and the second arm on a second end; and
a foot plate assembly comprising:
a foot plate;
an adjustment base coupled to a bottom surface of the foot plate;
an adjustment screw rotatably coupled to the adjustment base; and
a foot plate compressor bar coupled to the adjustment screw.

14. The joint compression device of claim 13, wherein the foot plate compressor bar comprises:
a base member with a first end and a second end;
a first through hole extending through the base member;
a plurality of second through holes positioned toward the first end of the base member; and
a plurality of third through holes positioned toward the second end of the base member, wherein the first through hole extends through the base member perpendicular to the plurality of second through holes and the plurality of third through holes.

15. The joint compression device of claim 13, wherein the foot plate compressor bar comprises:
a base with a first end and a second end;
a first securement member;
a first arm, wherein the first securement member is positioned between the base and the first arm;
a second securement member; and
a second arm, wherein the second securement member is positioned between the base and the second arm.

16. The joint compression device of claim 15, wherein the foot plate compressor bar further comprises:
a first spring positioned between the first securement member and the first arm; and
a second spring positioned between the second securement member and the second arm.

17. A The joint compression device, comprising:
a base system, comprising:
a first member;
a second member; and
at least one parallel member coupling the first member to the second member, wherein the second member translates along the at least one parallel member;
at least one arm coupled to the base system, wherein the at least one arm comprises:
a first arm coupled to the first member; and
a second arm coupled to the second member;
a set screw coupled to a bone plate;
a foot engagement member coupled to the second arm; and
a threaded knob rotatably coupled to the foot engagement member to secure the foot engagement member at a desired position.

18. The joint compression device of claim 17, further comprising:
a drill guide tube for insertion into a through hole of the foot engagement member; and
a guide wire tube for insertion into a through hole of the drill guide tube.

19. The joint compression device of claim 17, wherein the foot engagement member is concave and has a semi-circular shape.

20. The joint compression device of claim 17, wherein the foot engagement member is concave and has a circular shape.

* * * * *